(12) United States Patent
Bonutti et al.

(10) Patent No.: US 7,429,266 B2
(45) Date of Patent: *Sep. 30, 2008

(54) METHOD OF USING ULTRASONIC VIBRATION TO SECURE BODY TISSUE

(75) Inventors: Peter M. Bonutti, Effingham, IL (US); Matthew J. Cremens, Effingham, IL (US); Kevin Ruholl, Teutopolis, IL (US)

(73) Assignee: Marctec, LLC, Effingham, IL (US)

( * ) Notice: Subject to any disclaimer, the term of this patent is extended or adjusted under 35 U.S.C. 154(b) by 294 days.

This patent is subject to a terminal disclaimer.

(21) Appl. No.: 10/458,117

(22) Filed: Jun. 10, 2003

(65) Prior Publication Data

US 2003/0225438 A1 Dec. 4, 2003

Related U.S. Application Data

(62) Division of application No. 10/076,919, filed on Feb. 15, 2002, now Pat. No. 6,585,750, which is a division of application No. 09/524,397, filed on Mar. 13, 2000, now Pat. No. 6,368,343.

(51) Int. Cl.
    *A61B 17/04* (2006.01)
(52) U.S. Cl. .................................................. 606/232
(58) Field of Classification Search .................. 606/232, 606/233, 228
    See application file for complete search history.

(56) References Cited

U.S. PATENT DOCUMENTS 3,513,848 A 5/1970 Winston et al.

(Continued)

FOREIGN PATENT DOCUMENTS

EP 1614525 1/2006

(Continued)

OTHER PUBLICATIONS

Article entitled "Problem Solving Report Question No. 1014984.066", Ultrasonic Welding, Copyright 1999 NERAC Inc., Dec. 15, 1999.
Brochure entitled "Guide to Ultrasonic Plastic Assembly", Dukane Corporation, Ultrasonic Division, Publication date unknown.
Branson Technolog TL 4, Article entitled "Textured Surface Technology" Branson Ultrasonics Corp., Copyright 1992.

*Primary Examiner*—Michael J. Hayes
*Assistant Examiner*—Christina Gettman
(74) *Attorney, Agent, or Firm*—Fleit Gibbons Gutman Bongini & Bianco; Paul D. Bianco; Martin Fleit

(57) ABSTRACT

A suture and a suture retainer are positioned relative to body tissue. Ultrasonic vibratory energy is utilized to heat the suture retainer and effect a bonding of portions of the suture retainer to each other and/or to the suture. Portions of the body tissue may be pressed into linear apposition with each other and held in place by cooperation between the suture and the suture retainer. The suture retainer may include one or more portions between which the suture extends. The suture retainer may include sections which have surface areas which are bonded together. If desired, the suture may be wrapped around one of the sections of the suture retainer. The suture retainer may be formed with a recess in which the suture is received. If desired, the suture retainer may be omitted and the sections of the suture bonded to each other.

30 Claims, 9 Drawing Sheets

U.S. PATENT DOCUMENTS

| | | | |
|---|---|---|---|
| 3,657,056 A | 4/1972 | Wintson et al. |
| 3,918,442 A | 11/1975 | Nikolaev et al. |
| 4,662,068 A | 5/1987 | Polonsky |
| 4,662,887 A | 5/1987 | Turner et al. |
| 5,009,664 A | 4/1991 | Sievers |
| 5,120,175 A | 6/1992 | Arbegast et al. |
| 5,163,960 A | 11/1992 | Bonutti |
| 5,290,281 A | 3/1994 | Tschakaloff |
| 5,383,883 A | 1/1995 | Wilk et al. |
| 5,413,585 A | 5/1995 | Pagedas |
| 5,593,425 A | 1/1997 | Bonutti et al. |
| 5,628,751 A | 5/1997 | Sander et al. |
| 5,643,274 A | 7/1997 | Sander et al. |
| 5,713,903 A | 2/1998 | Sander et al. |
| 5,720,753 A | 2/1998 | Sander et al. |
| 5,735,875 A * | 4/1998 | Bonutti et al. .............. 606/232 |
| 5,836,897 A | 11/1998 | Sakural et al. |
| 5,879,372 A | 3/1999 | Bartlett |
| 5,891,166 A | 4/1999 | Schervinsky |
| 5,893,880 A | 4/1999 | Egan et al. |
| 5,906,625 A | 5/1999 | Bito et al. |
| 5,919,215 A | 7/1999 | Wiklund et al. |
| 5,928,244 A | 7/1999 | Tovey et al. |
| 5,941,901 A | 8/1999 | Egan |
| 5,964,765 A | 10/1999 | Fenton, Jr. et al. |
| 5,993,477 A | 11/1999 | Valitekunas et al. |
| 6,010,525 A | 1/2000 | Bonutti et al. |
| 6,056,751 A | 5/2000 | Fenton |
| 6,059,817 A | 5/2000 | Bonutti et al. |
| 6,059,827 A | 5/2000 | Fenton |
| 6,066,151 A | 5/2000 | Miyawaki et al. |
| 6,066,160 A * | 5/2000 | Colvin et al. ............... 606/232 |
| 6,080,161 A | 6/2000 | Eaves, III et al. |
| 6,099,537 A | 8/2000 | Sugai et al. |
| 6,106,545 A | 8/2000 | Egan |
| 6,139,320 A | 10/2000 | Hahn |
| 6,149,669 A | 11/2000 | Li |
| 6,174,324 B1 * | 1/2001 | Egan et al. ................... 606/232 |
| 6,179,840 B1 | 1/2001 | Bowman |
| 6,217,591 B1 | 4/2001 | Egan et al. |
| 6,273,717 B1 | 8/2001 | Hahn et al. |
| 6,286,746 B1 | 9/2001 | Egan et al. |
| 6,358,271 B1 | 3/2002 | Egan et al. |
| 6,409,743 B1 | 6/2002 | Fenton |
| 6,423,088 B1 | 7/2002 | Fenton |
| 6,488,196 B1 | 12/2002 | Fenton |
| 6,545,390 B1 | 4/2003 | Hahn et al. |
| 6,554,852 B1 | 4/2003 | Oberlander |
| 6,585,750 B2 | 7/2003 | Bonutti |
| 6,592,609 B1 | 7/2003 | Bonutti |
| 6,605,090 B1 | 8/2003 | Trieu et al. |
| 6,610,080 B2 | 8/2003 | Morgan |
| 6,635,073 B2 | 10/2003 | Bonutti |
| 6,666,877 B2 | 12/2003 | Morgan et al. |
| 6,669,705 B2 | 12/2003 | Westhaver et al. |
| 6,722,552 B2 | 4/2004 | Fenton |
| 6,786,989 B2 | 9/2004 | Torriani et al. |
| 6,893,434 B2 | 5/2005 | Fenton et al. |
| 6,913,666 B1 | 7/2005 | Aeschlimann et al. |
| 6,921,264 B2 | 7/2005 | Mayer et al. |
| 6,923,824 B2 | 8/2005 | Morgan et al. |
| 6,955,540 B2 | 10/2005 | Mayer et al. |
| 7,001,411 B1 | 2/2006 | Dean |
| 7,008,226 B2 | 3/2006 | Mayer et al. |
| 7,090,111 B2 | 8/2006 | Egan et al. |
| 7,160,405 B2 | 1/2007 | Aeschlimann et al. |
| 2003/0118518 A1 | 6/2003 | Hahn et al. |

FOREIGN PATENT DOCUMENTS

JP    8-140982    6/1996

* cited by examiner

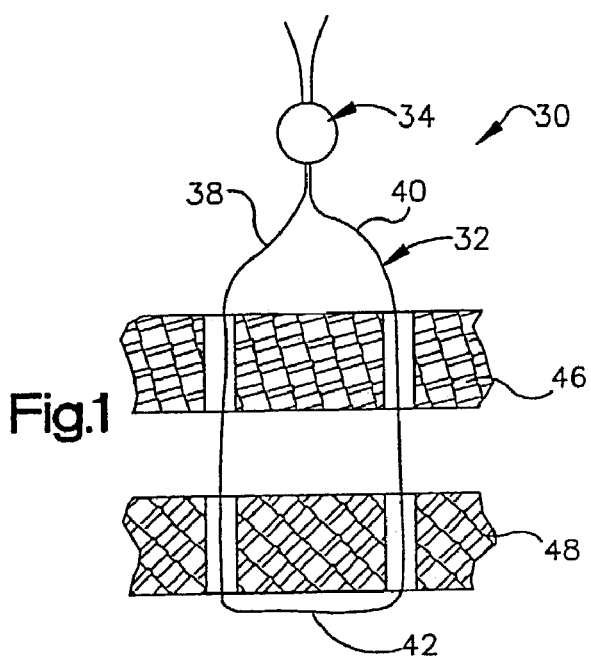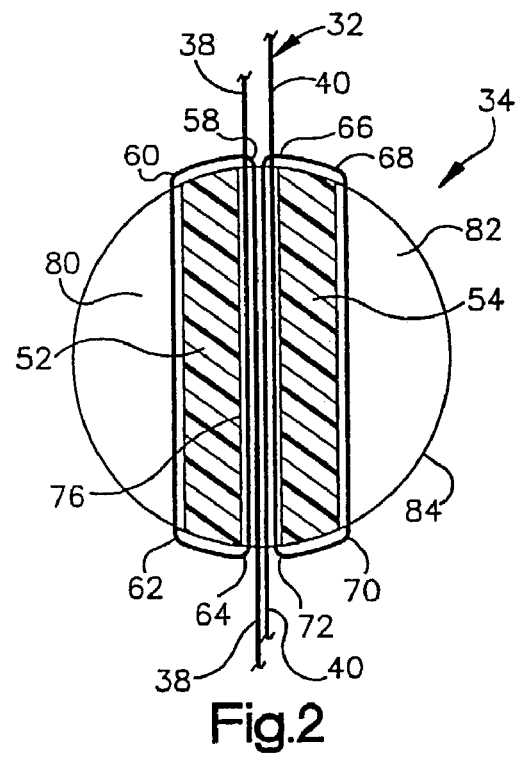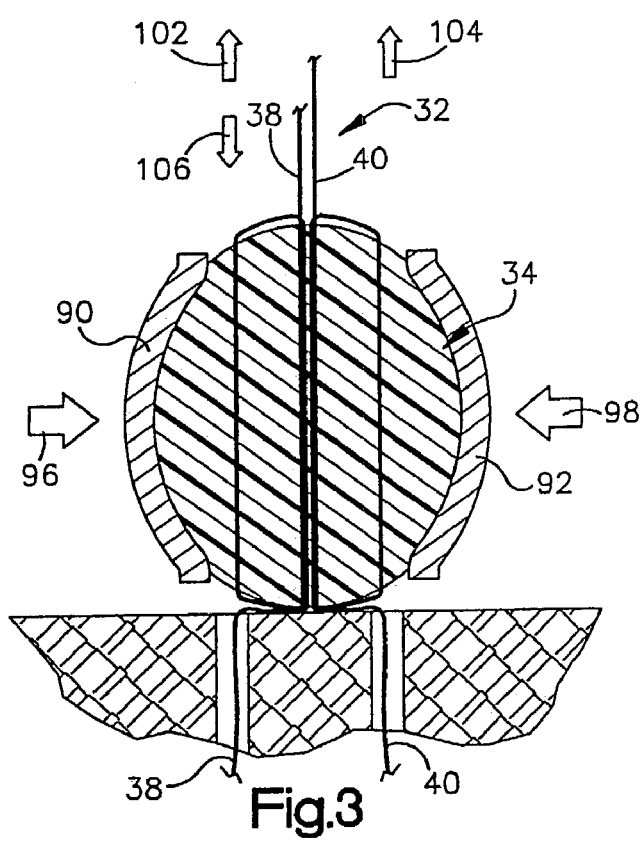

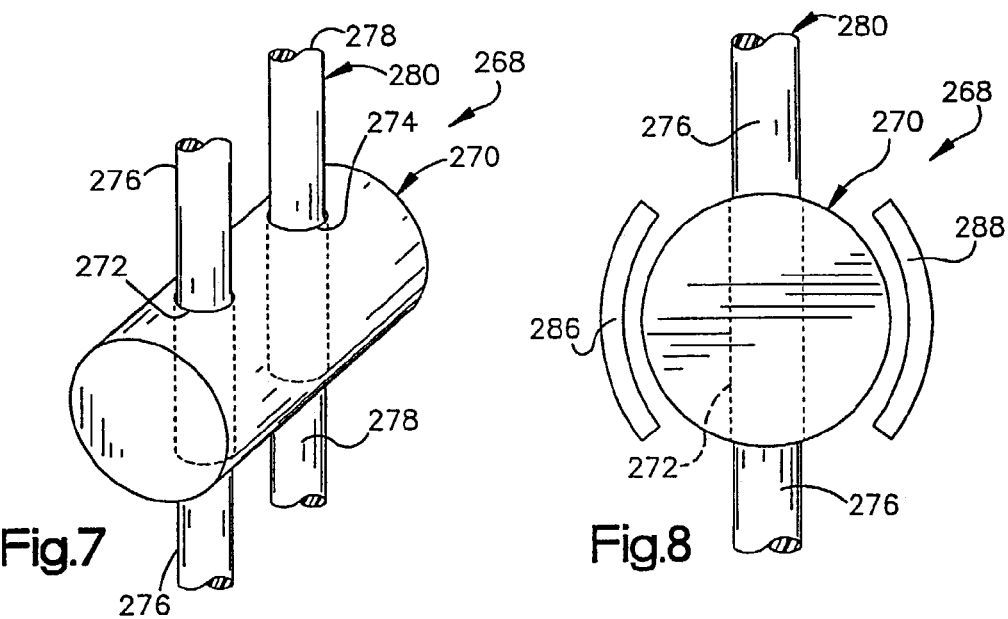
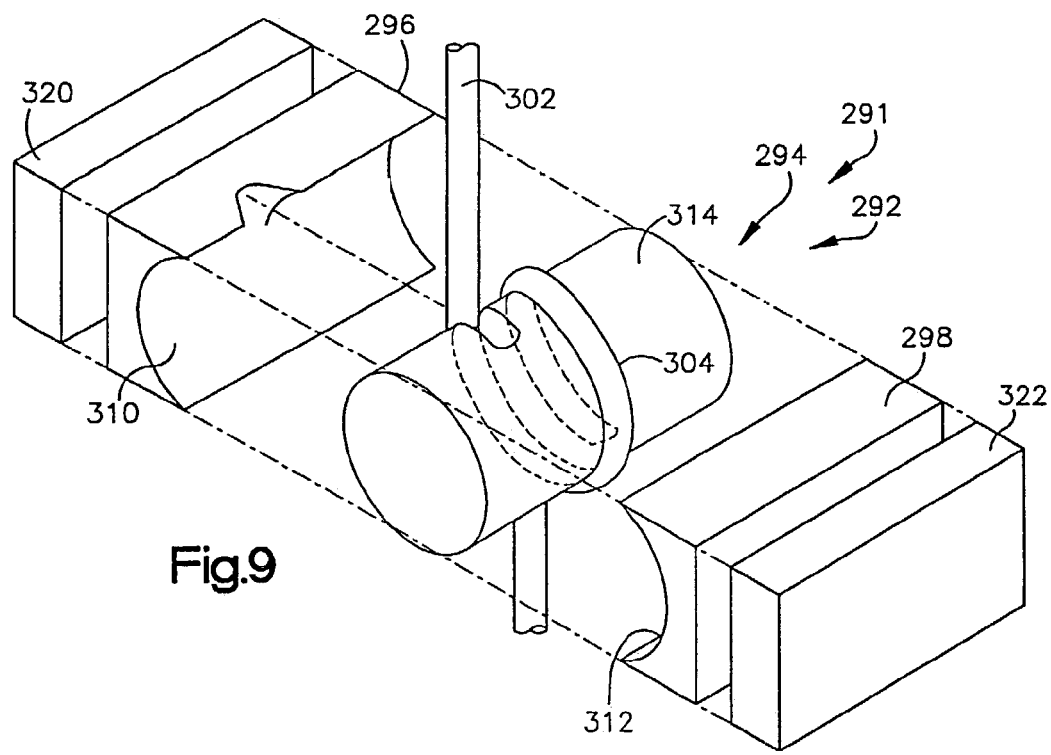

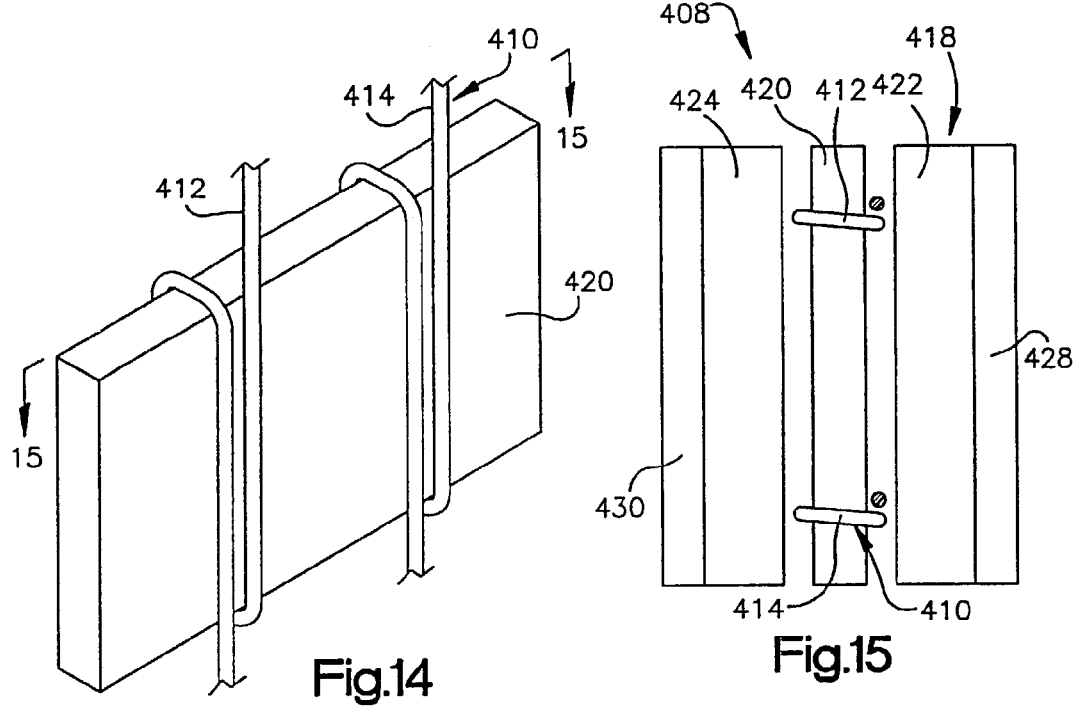
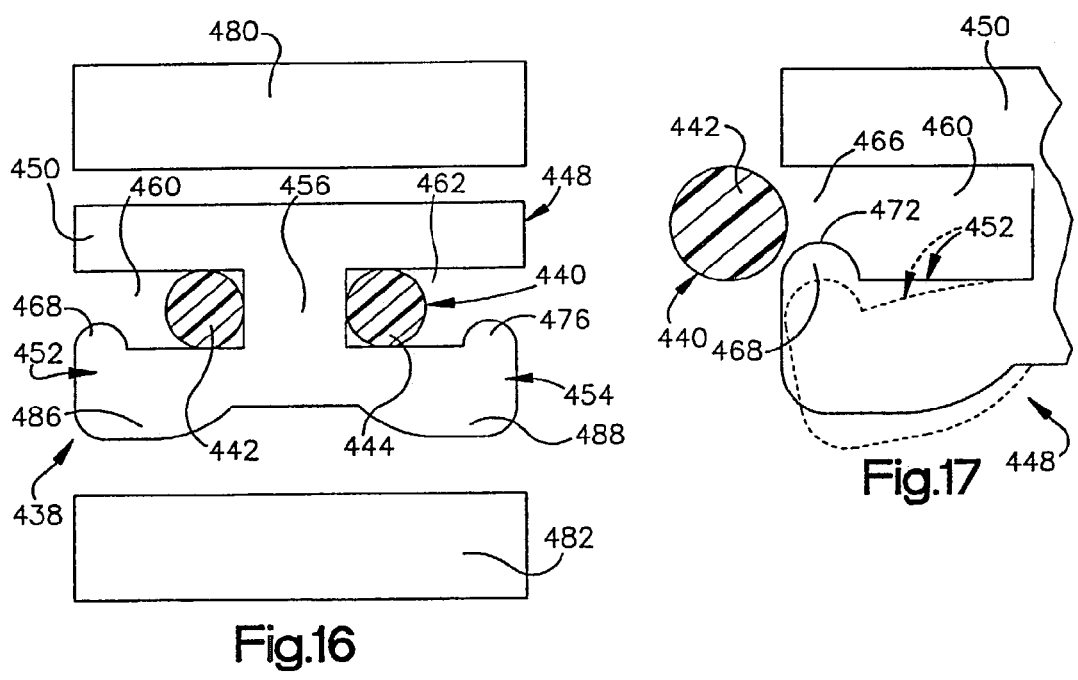

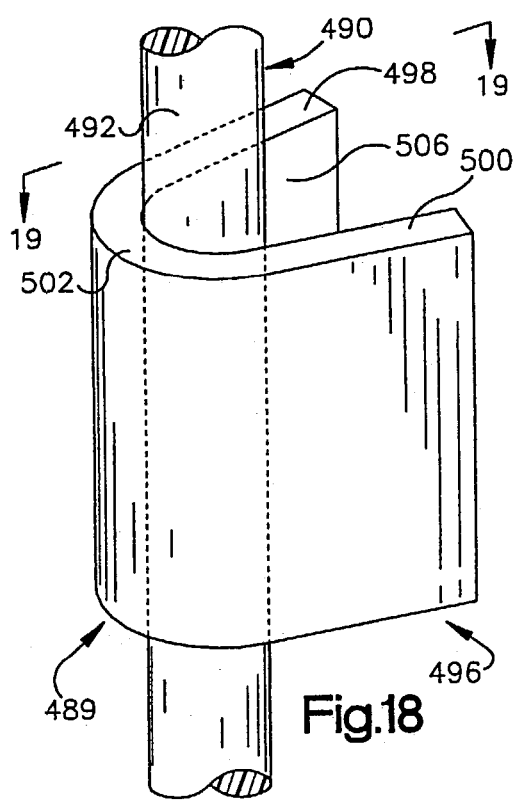
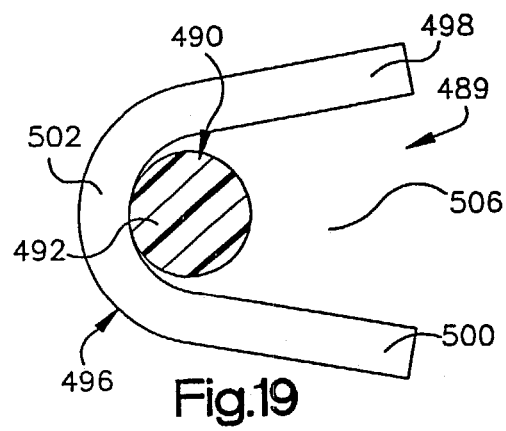
Fig.19
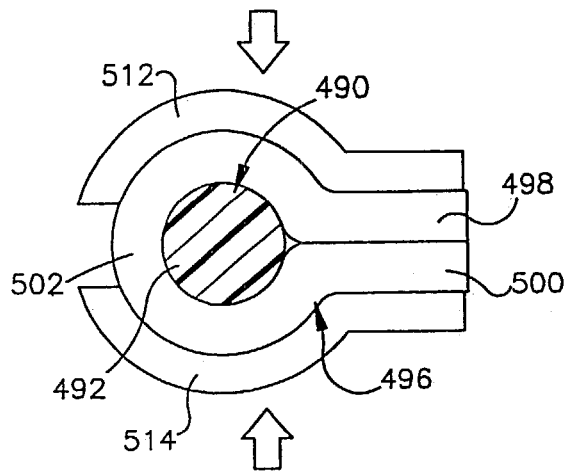
Fig.20
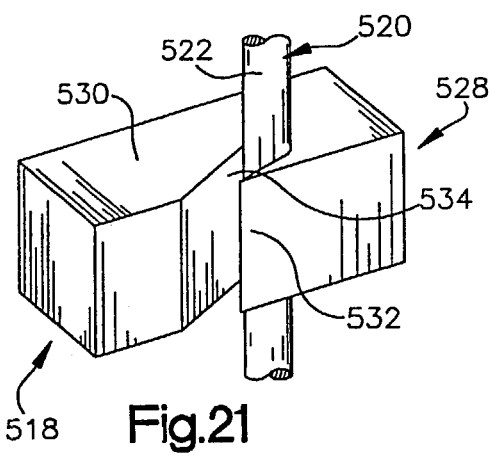
Fig.21
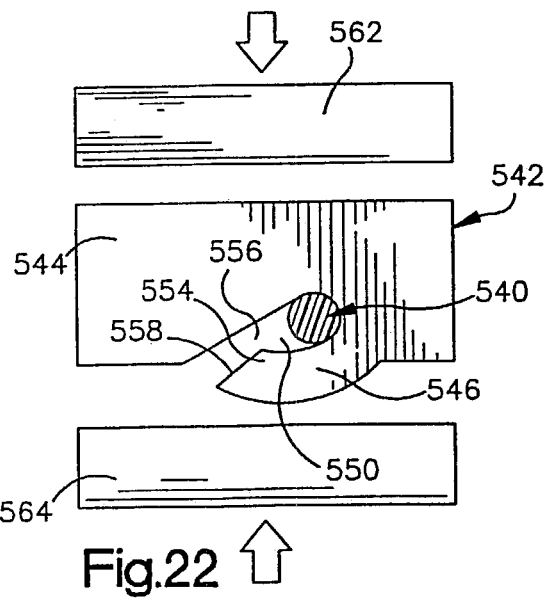
Fig.22

METHOD OF USING ULTRASONIC VIBRATION TO SECURE BODY TISSUE

CROSS REFERENCE TO RELATED APPLICATIONS

This application is a divisional of U.S. patent application Ser. No. 10/076,919, filed Feb. 15, 2002, now U.S. Pat. No. 6,585,750, which is a divisional of U.S. patent application Ser. No. 09/524,397, filed Mar. 13, 2000, now U.S. Pat. No. 6,368,343.

FIELD OF THE INVENTION

The present invention relates to a new and improved method of securing body tissue by using ultrasonic vibratory energy.

BACKGROUND OF THE INVENTION

Difficulty has been encountered in securing sutures against movement relative to body tissue. A knot may be tied in a suture to prevent loosening of the suture. However, the knot weakens a portion of the suture and reduces the overall force transmitting capability of the suture. It has been suggested that a suture could be secured using a suture retainer in the manner disclosed in U.S. Pat. Nos. 5,735,875 and 6,010,525.

When a suture retainer is used to maintain a suture in a desired position relative to body tissue, the material of the suture retainer may be pressed against the suture. During pressing of the material of the retainer against the suture, the suture may be heated to promote a flowing of the material of the suture retainer and bonding to the material of the suture retainer to the surface of the suture by heating material of the suture retainer into its transition temperature range.

When the material of the suture retainer is heated into its transition temperature range, the material changes from a solid condition in which it has a fixed form to a soft or viscous condition. When the material of a suture retainer has been heated into the transition temperature range, the material can be molded around an outer side surface of a suture and bonded to the suture without significant deformation of the suture. The transition temperature ranges for various polymers which are suitable for forming suture retainers are disclosed in the aforementioned U.S. Pat. No. 5,735,875.

SUMMARY OF THE INVENTION

The present invention provides a new and improved method for use in securing body tissue. If desired, a suture retainer may be used to grip the suture. When a suture retainer is used, ultrasonic vibratory energy is transmitted to the material of the suture retainer to effect a heating of at least some of the material of the suture retainer. Portions of the suture retainer are then bonded to each other and/or to the suture.

It may be desired to retain layers of body tissue in linear apposition with each other. When this is to be done, a suture is used to hold the layers of body tissue in linear apposition after they have been approximated to each other. The suture may be secured relative to the body tissue by a suture retainer or crimp. Alternatively, sections of the suture may be secured together. To secure the suture relative to the body tissue, ultrasonic vibratory energy is applied to either the suture or the suture retainer. The ultrasonic energy may be applied while the suture is being tensioned with a predetermined force and while a predetermined force is being transmitted to the body tissue.

The suture retainer or crimp may have any one of many different constructions. One specific suture retainer constructed in accordance with one of the features of the present invention includes one or more passages through which one or more sections of the suture are inserted. In another embodiment of the invention, the suture retainer has sections which are formed separately from each other. The sections of the suture retainer are connected with the suture and/or each other by transmitting ultrasonic vibratory energy to at least one of the sections of the suture.

If desired, the suture may be wrapped around a portion of the suture retainer. The suture retainer may be provided with one or more recesses into which one or more sections of the suture are moved. The transmission of ultrasonic vibratory energy to the suture retainer is utilized to effect a bonding of portions of the suture retainer with each other and/or with the suture.

The suture retainer may be omitted and sections of the suture bonded to each other. When this is to be done, ultrasonic vibratory energy is transmitted to the sections of the suture. Force is applied against opposite sides of the sections of the suture to increase the extent of the sections of the suture in a direction transverse to the sections of the suture. As the transverse extent of the suture is increased, areas on outer side surfaces of the sections of the suture are increased.

BRIEF DESCRIPTION OF THE DRAWINGS

The foregoing and other features of the invention will become more apparent upon a consideration of the following description taken in connection with the accompanying drawings wherein:

FIG. 1 is a schematic illustration depicting the manner in which layers of body tissue are moved into linear apposition with each other and secured with a suture and suture retainer;

FIG. 2 is a schematic fragmentary sectional view illustrating the manner in which the suture and suture retainer of FIG. 1 are positioned relative to each other;

FIG. 3 is a fragmentary schematic illustration depicting the manner in which ultrasonic vibratory energy is applied to the suture retainer of FIG. 2;

FIG. 7 is a schematic pictorial illustration of an embodiment of the invention in which a suture retainer has a pair of passages for receiving sections of a suture;

FIG. 8 is a schematic illustration depicting the manner in which ultrasonic vibratory energy is applied to the suture retainer of FIG. 7;

FIG. 9 is an exploded fragmentary schematic illustration of another embodiment of the invention and depicting the manner in which a suture is wrapped around a section of a suture retainer and the relationship of apparatus for applying ultrasonic vibratory energy to sections of the suture retainer;

FIG. 14 is a schematic illustration of another embodiment of the invention and depicting the manner in which sections of a suture are wrapped around a section of a suture retainer;

FIG. 15 is a schematic sectional view, taken generally along the line 15-15 of FIG. 14, illustrating the relationship between sections of the suture retainer and an apparatus for applying ultrasonic vibratory energy to the suture retainer;

FIG. 16 is a schematic plan view of another embodiment of the invention, illustrating the relationship of sections of a suture to recesses formed in a suture retainer which is disposed between portions of an apparatus for applying ultrasonic vibratory energy to the suture retainer;

FIG. 17 is an enlarged fragmentary schematic illustration depicting the manner in which a section of the suture is moved into one of the recesses in the suture retainer of FIG. 16;

FIG. 18 is a schematic pictorial illustration depicting the manner in which another embodiment of the suture retainer is positioned relative to the suture;

FIG. 19 is a plan view, taken generally along the line 19-19 of FIG. 18, illustrating the relationship between the suture retainer and the suture;

FIG. 20 is a plan view, generally similar to FIG. 19, illustrating the relationship of an apparatus for applying ultrasonic vibratory energy to the suture retainer and the suture retainer and suture of FIG. 19;

FIG. 21 is a schematic pictorial illustration of an embodiment of the suture retainer having a recess which receives a portion of a suture;

FIG. 22 is a plan view of another embodiment of the invention and illustrating the manner in which a suture is positioned in a recess in the suture retainer and the relationship of apparatus for applying ultrasonic vibratory energy to the suture retainer;

DETAILED DESCRIPTION OF THE INVENTION

Embodiment of FIG. 1-3

Figure 4:
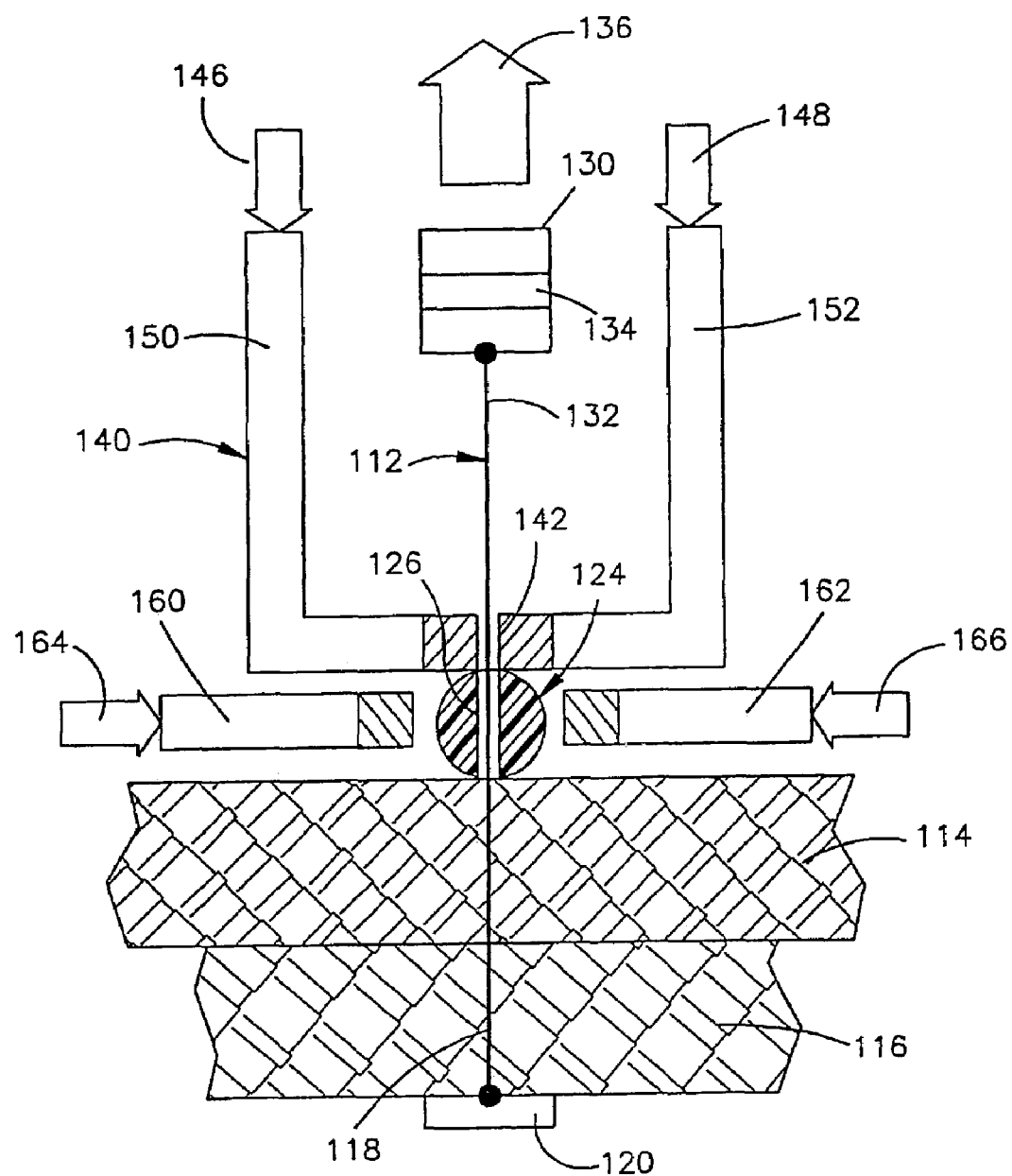
FIG. 4 is a schematic fragmentary sectional view of another embodiment of the invention and illustrating the approximation of layers of tissue by tensioning a suture with a predetermined force and pressing a suture retainer against the body tissue with a predetermined force.

A tissue securing system 30 (FIG. 1) includes a suture 32 and a suture retainer or crimp 34. The suture 32 includes left and right sections 38 and 40 which are interconnected by a connector section 42. The suture retainer 34 grips the left and right sections 38 and 40 of the suture 32.

The tissue securing system 30 is used in a sterile, operating room environment to secure upper and lower layers 46 and 48 of soft, human body tissue in linear apposition with each other. Thus, the two layers 46 and 48 of human body tissue are approximated and held against movement relative to each other by the suture 32. Although the two layers 46 and 48 of body tissue have been schematically illustrated in FIG. 1 as being spaced apart from each other, they are held in a side-by-side relationship with each other and pressed together by tightening the tissue securing system 30. Pressing the two layers 46 and 48 together with the tissue securing system 30 promotes healing of the tissue.

Although the tissue securing system 30 has been illustrated in FIG. 1 as being used to hold layers of soft tissue in linear apposition with each other, it is contemplated that the tissue securing system may be used in many different locations in a patient's body to secure tissue. For example, the tissue securing system 30 could be utilized to secure soft tissue, such as a ligament or tendon, against movement relative to a bone. Alternatively, the tissue securing system 30 could be utilized to interconnect portions of a flexible conduit, such as a blood vessel or intestine. It should be understood that the tissue securing system 30 may be used with either hard body tissue, or soft body tissue, or both hard and soft body tissue.

If desired, a force distribution member, such as a button, could be utilized between the connector section 42 of the suture 32 and the lower layer 48 of body tissue. The force distribution member would distribute force over a relative large area of the lower layer 48 of body tissue. Similarly, a force distribution member, such as a button, could be utilized between the upper layer 46 of soft tissue and the left and right sections 38 and 40 of the suture 32 and the suture retainer 34.

It is also contemplated that the suture 32 could extend through a suture anchor and/or be connected with body tissue in a manner similar to that disclosed in U.S. Pat. Nos. 5,584,862; 5,549,631; and/or 5,527,343. Of course, the suture 32 could be connected with body tissue in a different manner if desired. For example, the connector section 42 could be eliminated. If this is done, the left section 38 of the suture 32 could be connected with one suture anchor and the right section 40 of the suture could be connected with a second suture anchor.

Although the sections 38 and 40 of the suture 32 could extend straight through the suture retainer 34, in the illustrated embodiment of the invention, the sections 38 and 40 of the suture 32 are wrapped around portions of the suture retainer 34. Thus, the left section 38 of the suture 32 is wrapped around a portion 52 (FIG. 2) of the suture retainer 34. Similarly, the right section 40 of the suture is wrapped around a portion 54 of the suture retainer 34.

In the illustrated embodiment of the invention, the left section 38 of the suture 32 is wrapped for more than a complete turn around the portion 52 of the suture retainer and the right section 40 of the suture is wrapped for more than a complete turn around the portion 54 of the suture retainer.

However, if desired, wrapping of the sections 38 and 40 of the suture 32 around the suture retainer 34 could be omitted or each of the sections of the suture could be wrapped for less than one complete turn around a portion of the suture retainer.

When the sections 38 and 40 of the suture 32 are wrapped around the portions 52 and 54 of the suture retainer 34, a plurality of bends are formed in each of the sections of the suture. Thus, bends 58, 60, 62 and 64 are formed in the section 38 of the suture 32 as it is wrapped around the portion 52 of the suture retainer 34. Similarly, bends 66, 68, 70 and 72 are formed in the section 40 of the suture 32 as it is wrapped around the portion 54 of the suture retainer 34. Of course, a greater number of bends would be formed in each of the sections 38 and 40 of the suture 32 if they were wrapped a greater number of times around the suture retainer 34.

Although the suture retainer 34 could have many different constructions and configurations, in the illustrated embodiment of the invention, the suture retainer 34 is integrally formed as one piece and has a spherical configuration. A cylindrical central passage 76 extends axially through the suture retainer 34 between upper and lower (as viewed in FIG. 2) polar regions of the spherical suture retainer. The two sections 38 and 40 of the suture 32 extend through the passage 76. The suture retainer 34 is formed separately from the suture 32 and is initially disconnected from the suture.

In the illustrated embodiment of the invention, two lengths of the left suture section 38 and two lengths of the right suture section 40 extend through the passage 76 as a result of the wrapping of the sections of the suture around the portions 52 and 54 of the suture retainer 34. However, the two sections 38 and 40 of the suture 32 could extend straight through the passage 76 without being wrapped around the portions 52 and 54 of the suture retainer 34. If this was done, only a single length of the left section 38 of the suture 32 would be disposed in the passage 76 adjacent to a single length of the right section 40 of the suture 32. Of course, if the sections 38 and 40 of the suture 32 were wrapped around the portions 52 and 54 of the suture retainer for a greater number of turns, a greater number of lengths of the sections 38 and 40 of the suture 32 would extend through the passage 76.

In the illustrated embodiment of the suture retainer 34, a pair of grooves or recesses 80 and 82 extend radially inward from a spherical outer side surface 84 of the suture retainer 34. The grooves or recesses 80 and 82 are relatively deep so that the portions 52 and 54 of the suture retainer around which the suture is wrapped are relatively slender. This results in relatively short lengths of the sections 38 and 40 of the suture being disposed in engagement with the outer side surface of the suture retainer 34 adjacent to the upper and lower polar regions of the suture retainer.

In the embodiment of the invention illustrated in FIG. 2, the grooves or recesses 80 and 82 extend inward from the outer side surface 84 of the suture retainer 34. The depth of the grooves or recesses 80 and 82 varies along the vertical (as viewed in FIG. 2) length of the grooves. However, it is contemplated that the grooves 80 and 82 could be constructed so as to have a uniform depth throughout their length. If this was done, the grooves 80 and 82 would have an arcuate configuration with centers of curvature which are coincident with the center of curvature of the spherical outer side surface 84 of the suture retainer 34.

Rather than opening radially outward to the outer side surface 84 of the suture retainer 34, the grooves 80 and 82 could be undercut to enclose the portions of the suture 32 disposed in the grooves. It is contemplated that the grooves could have any one of the groove configurations disclosed in U.S. Pat. No. 6,010,525. The disclosure from the aforementioned U.S. Pat. No. 6,010,525 is incorporated herein in its entirety by this reference thereto. Alternatively, the grooves 80 and 82 could be formed as passages which extend through the suture retainer 34 parallel to and spaced apart from the central passage 76.

It is contemplated that the suture retainer 34 may be formed of many different materials. However, it is contemplated that it will be preferred to form the suture retainer 34 of a biodegradable polymer. One biodegradable polymer which may be utilized is polycaperlactone. Alternatively, the suture retainer 34 could be formed of polyethylene oxide terephthalate or polybutylene terephthalate. The suture retainer 34 could be formed as a polyhydroxyalkanoate if desired. It is also contemplated that other biodegradable or other bioerodible copolymers could be utilized if desired.

Although it is preferred to form the suture retainer 34 of a biodegradable material, the suture retainer could be formed of a material which is not biodegradable. For example, the suture retainer 34 could be formed of an acetyl resin, such as "Delrin" (trademark). Alternatively, the suture retainer 34 could be formed of a para-dimethylamino-benzenediazo sodium sulfonate, such as "Dexon" (trademark). If desired, the suture retainer 34 could be formed of nylon.

The suture 32 may be formed of the same material as the suture retainer 34 or of a different material. The suture 32 may be formed of natural or synthetic materials. The suture 32 may be a monofilament or may be formed of a plurality of interconnected filaments. The suture 32 may be biodegradable or non-biodegradable. It is contemplated that the suture retainer 34 could be utilized in association with force transmitting elements other than a suture. It is believed that it may be preferred to form the suture 32 of the same material as the suture retainer 34.

In accordance with a feature of the present invention, ultrasonic vibratory energy is utilized to cause the suture retainer 34 to grip the suture 32. The ultrasonic vibratory energy is at a frequency above that which can normally be detected by the human ear, that is, above 16 to 20 kilohertz. Although there are a wide range of frequencies which may be utilized, it is believed that it will be desirable to use ultrasonic energy having a frequency of between 20 kilohertz and 70 kilohertz. However, higher frequency vibratory energy could be utilized if desired.

The ultrasonic vibratory energy may be continuously applied, pulsed or modulated in various fashions. Any one of many known transducers may be utilized to change electrical energy into mechanical vibrations having an ultrasonic frequency. The transducers may be piezoelectric, ferroelectric, or magnetostrictive. One commercial source of apparatus which may be utilized to provide ultrasonic vibratory energy is Dukane Corporation, Ultrasonics Division, 2900 Dukane Drive, St. Charles, Ill. Of course, there are other sources of apparatus which can be utilized to provide ultrasonic vibratory energy.

The ultrasonic vibratory energy creates frictional heat at the areas where the suture retainer 34 and suture 32 are disposed in engagement with each other. The frictional heat provided by the ultrasonic vibratory energy is effective to heat the material of the suture retainer 34 into its transition temperature range while the material of the suture 32 remains at a temperature close to or below its transition temperature range. For example, the suture 32 may be formed of a material having a transition temperature range which is above 190 degrees Celsius. The suture retainer 34 may have a transition temperature range which, for the most part, is at a temperature below 190 degrees Celsius.

However, it should be understood that at least a portion or even the entire transition temperature range for the suture 32 could be co-extensive with the transition range for the suture retainer 34. In fact, the transition temperature range of the suture 32 could extend below the transition temperature range of the suture retainer 34. However, it is believed that it may be preferred to have the transition temperature range for the suture 32 above at least a portion of the transition temperature range of the suture retainer 34.

Once the material of the suture retainer 34 has been heated into its transition temperature range by the ultrasonic vibratory energy, the plastic material of the suture retainer 34 loses its rigidity and becomes soft and viscous. The softened material of the suture retainer is moldable and flows, when subjected to pressure, around the suture 32 without significant deformation of the suture. However, the temperature range into which the suture 32 is heated and the pressure applied against the suture may result in some deformation of the suture.

Although it is contemplated that the suture 32 and suture retainer 34 could be made of many different materials, the suture and suture retainer may be formed of a plastic material which is a biopolymer. For example, the suture 32 and/or suture retainer 34 may be formed of polyglycolide which is commercial available under the trademark "Dexon". Polyglycolide is a crystalline material that melts at about 225° Celsius. However, the suture could be formed of a glycolide-based copolymer which is commercially available under the trademark "Vicryl".

The suture retainer 34 is also made of a plastic material which may be a biopolymer. For example, the suture retainer 34 may be made of polydellactide. The transition temperature of polydellactide will vary depending upon the specific characteristics of the material. However, a suture retainer 34 formed of polydellactide may have a transition temperature range of about 75° Celsius to about 120° Celsius. Other materials which may be utilized for forming the suture 32 and/or suture retainer 34 are disclosed in U.S. Pat. No. 5,735,875. The disclosure in the aforementioned U.S. Pat. No. 5,735,875 is hereby incorporated herein in its entirety by this reference thereto.

In order to promote bonding of the material of the suture retainer 34 to the suture 32, both the suture and suture retainer may be formed of the same amorphous thermoplastic material. For example, both the suture 32 and suture retainer 34 may be formed of a polyhydroxy-alkanoate. Alternatively, both the suture 32 and suture retainer 34 may be formed of nylon. It is contemplated that the suture 32 and suture retainer 34 could be formed of different amorphous polymers which are similar, that is, have the same or similar chemical properties.

When the ultrasonic vibratory energy is to be applied to the suture retainer 34, a supportive member or anvil 90 (FIG. 3) is positioned in engagement with one side of the suture retainer 34. A horn or acoustic tool 92 is positioned in engagement with the opposite side of the suture retainer 34. Force, indicated schematically by arrows 96 and 98 in FIG. 3, is applied against the suture retainer 34 by the anvil 90 and horn 92.

The horn is vibrated, horizontally as viewed in FIG. 3, at a rate in excess of 20 kilohertz. Although the horn 92 may be vibrated at any desired frequency within range of 20 kilohertz to 70 kilohertz, it is believed that it may be desirable to vibrate the horn 92 at a rate which is close to or greater than 70 kilohertz. The horn 92 is vibrated for a dwell time which is sufficient to transmit enough ultrasonic vibratory energy to the suture retainer 34 to heat at least a portion of the material of the suture retainer 34 into its transition temperature range.

To effect a heating of the material of the suture retainer 34, mechanical vibrations are transmitted from the horn 92 through the material of the retainer 34 to a location adjacent to an interface between the suture 32 and the suture retainer 34. The frictional heat created by the ultrasonic vibratory energy transmitted to the suture retainer from the horn 92 is sufficient to heat the material of the suture retainer 34 at locations adjacent to the suture 32, into the transition temperature range of the material of the suture retainer. As this occurs, the passage 76 and grooves 80 and 82 collapse under the influence of the force indicated at 96 and 98 in FIG. 3 and the ultrasonic vibratory energy transmitted from the horn 92.

The vibration of the horn 92 is then interrupted and the material of the suture retainer 34 begins to cool. The clamping force, indicated by the arrows 96 and 98, is maintained against opposite sides of the suture retainer 34 by the anvil 90 and horn 92 during the time which ultrasonic vibratory energy is transmitted from the horn 92 to the material of the suture retainer 34. After interruption of the transmission of ultrasonic vibratory energy, the clamping force, indicated schematically by the arrows 96 and 98 and applied by the anvil 90 and horn 92, is maintained for a predetermined amount of time sufficient to allow the material of the suture retainer to cool and bond to both itself and the suture 32.

If desired, the force, indicated schematically by the arrows 96 and 98 in FIG. 3, applied by the anvil 90 and horn 92 to the suture retainer 34 may be increased as the transmission of ultrasonic vibratory energy to the suture retainer 34 from the horn 92 is interrupted. The force, indicated schematically by the arrows 96 and 98 in FIG. 3, is sufficient to cause the passage 76 and recesses 80 and 82 to collapse as the suture retainer 34 is heated by ultrasonic vibratory energy and subsequently allowed to cool.

The length of time for which ultrasonic vibratory energy is transmitted to the suture retainer 34 may vary as a function of the amplitude and frequency of the ultrasonic vibratory energy transmitted to the suture retainer. It is contemplated that the frequency of the ultrasonic vibratory energy will be in a range of between 20 kilohertz and 70 kilohertz. It is contemplated that the amplitude of the ultrasonic vibrations may vary within a range of 0.0008 inches to 0.0050 inches depending upon the design of the suture retainer 34 and the material forming the suture retainer.

It is also contemplated that the force, indicated schematically by the arrows 96 and 98, applied against the suture retainer 34 may vary depending upon the construction of the suture retainer 34 and the material forming the suture retainer. For example, a force of approximately 115 pounds may be applied against the suture retainer 34 by both the anvil 90 and horn 92. However, the amount of force which is applied will probably be different for different suture retainers and different horns 92.

It is believed that the ultrasonic vibratory energy may be transmitted from the horn 92 to the suture retainer 34 for a period of time which varies between 0.25 seconds and 1.0 second. After the transmission of ultrasonic vibratory energy has been interrupted, the force, indicated by the arrows 96 and 98, may continue to be applied to the suture retainer 34 by the anvil 90 and horn 92 for approximately 1.0 seconds.

The extent to which the suture retainer 34 is compressed by the force 96 and 98 applied against the suture retainer by the anvil 90 and horn 92 has been illustrated schematically in FIG. 3. It is contemplated that the distance through which the anvil 90 and horn 92 move toward each other to compress the suture retainer 34 may be from 0.010 inches to 0.050 inches.

Of course, the distance through which the suture retainer 34 is compressed by the anvil 90 and horn 92 may be different for suture retainers having different constructions and/or formed of different materials.

It should be understood that the foregoing specific operating characteristics, for example, amplitude and frequency of the ultrasonic vibratory energy transmitted from the horn 92 to the suture retainer 34, force applied against the suture retainer by the anvil 90 and horn 92, time for which force and/or ultrasonic vibratory energy is applied, and the distance through which the suture retainer is compressed, have been set forth herein for purposes of clarity of description. It is contemplated that the foregoing specific numerical values will be different for different embodiments of the invention and may vary extensively from the exemplary values set forth.

When the two layers 46 and 48 of body tissue are to be held in position relative to each other by the tissue securing system 30, the suture 32 is positioned relative to the layers of body tissue. The left and right sections 38 and 40 of the suture 32 extend through the two layers 46 and 48 of tissue. Although the sections 38 and 40 of the suture 32 have been illustrated schematically in FIG. 1 as extending through passages in the layers 46 and 48 of body tissue, the passages could be omitted and the suture 32 sewn through the body tissue without forming passages in the body tissue.

In the embodiment of the invention illustrated in FIG. 1, the sections 38 and 40 of the suture 32 are interconnected by the connector section 42 which extends along one side of the layer 48 of body tissue. If desired, the sections 38 and 40 of the suture 32 could be connected with a single anchor embedded in either hard or soft body tissue. Alternatively, a separate anchor could be provided for each of the sections 38 and 40 of the suture 32. These anchors could be embedded in the body tissue or disposed adjacent to one side of the body tissue.

When the suture 32 has been positioned relative to the two layers 46 and 48 of body tissue, the two layers of body tissue are pressed against each other in linear apposition. The suture retainer 34 is then connected with the suture 32. When the suture retainer 34 is to be connected with the suture 32, the left (as viewed in FIG. 2) section 38 of the suture is inserted through the central passage 76 in the suture retainer 34. The left section 38 of the suture 32 is then wrapped around the portion 52 of the suture retainer 34 and again inserted through the central passage 76.

Similarly, the right section 40 of the suture 32 is inserted through the central passage 76 and wrapped around the portion 54 of the suture retainer 34. The right section 40 of the suture is then inserted through the central passage 76 for a second time. This results in the suture 32 being connected with the suture retainer 34 in the manner illustrated schematically in FIG. 2.

The suture retainer 34 is then moved downward (as viewed in FIGS. 1 and 2) along the suture 32 toward the upper layer 46 of body tissue. The suture 32 is tensioned with a predetermined force during downward movement of the suture retainer 34 toward the body tissue. As the suture retainer 34 moves downward (as viewed in FIGS. 1 and 2) along the suture 32 toward the upper layer 46 of body tissue, the turns formed in the sections of the suture around the portions 52 and 54 of the suture retainer 34 move downward toward the body tissue. Thus, the bends 58-64 in the section 38 of the suture 32 and the bends 66-72 in the section 40 of the suture 32 move along the suture toward the upper layer 46 of body tissue with the suture retainer 34.

As the suture retainer 34 is moved along the suture 32 toward the upper layer 46 of body tissue, a predetermined tension, indicated by arrows 102 and 104 in FIG. 3, is maintained in the sections 38 and 40 of the suture 32. The magnitude of the tension forces 102 and 104 in the sections 38 and 40 of the suture 32 is selected as a function of the characteristics of the layers 46 and 48 of body tissue and as a function of the strength of the suture.

As the suture retainer 34 moves downward (as viewed in FIGS. 1-3), the leading portion of the suture retainer moves into engagement with the upper layer 46 of body tissue (FIG. 3). The suture retainer 34 is then pressed against the upper layer 46 of body tissue. If desired, a force distribution member, such as a button, could be provided between the suture retainer 34 and the body tissue 46.

The suture retainer 34 is pressed downward against the body tissue 46 with a predetermined force, indicated schematically by an arrow 106 in FIG. 3, while a predetermined tension, indicated schematically by the arrows 102 and 104, is maintained in the suture 32. The force transmitted from the suture 32 and suture retainer 34 to the layers 46 and 48 of body tissue presses them together and, to some extent, compresses the layers of body tissue. This results in the layers of body tissue being held in linear apposition and being compressed to promote healing of the layers 46 and 48 of body tissue.

The force, indicated by the arrows 102 and 104, with which the sections 38 and 40 of the suture 32 are tensioned, may vary depending upon the material from which the suture is constructed and the size of the suture. By consulting a chart, a surgeon can select a suture size and strength suitable for a particular use. Thus, a relatively large suture having substantial strength may be selected when body tissue is to be connected with a bone or when portions of a bone are to be interconnected by the suture. On the other hand, a relatively small suture size having a relatively small strength may be selected when delicate body tissue, such as stomach or intestinal tissue, is to be interconnected with the suture. The tension forces 102 and 104 in the sections 38 and 40 are determined as a function of the strength 32 of the suture and the characteristics of the body tissue through which the suture extends.

The suture 34 is pressed against the body tissue with a force which is also a function of the size and strength of the suture 32 and the characterisatics of the body tissue 46 and 48. One way in which force with which the suture 32 is tensioned and with which the suture 34 is pressed against body tissue is disclosed in U.S. patent application Ser. No. 09/348,940 filed Jul. 7,1999 by Peter M. Bonutti et al. and entitled "Method and Apparatus for Securing a Suture". The disclosure in the aforementioned U.S. patent application Ser. No. 09/348,940, now U.S. Pat. No. 6,159,234, is hereby incorporated herein by this reference thereto.

After the suture retainer 34 has been pressed against the body tissue with a predetermined force and the suture 32 tensioned with a predetermined force to compress the layers 46 and 48 of body tissue, ultrasonic vibratory energy is applied to the suture retainer. To apply the ultrasonic vibratory energy to the suture retainer 34, the anvil 90 (FIG. 3) is positioned in engagement with one side of the suture retainer and the horn 92 is positioned in engagement with the opposite side of the suture retainer. The anvil 90 and horn 92 are urged toward each other with a predetermined force, indicated schematically by the arrows 96 and 98 in FIG. 3.

The specific magnitude of the force 96 and 98 will vary depending upon the composition of the suture retainer 34 and the construction of the suture retainer. In addition, the magnitude of the force 96 and 98 will vary as a function of the desired extent of deformation of the suture retainer 34. When the suture retainer 34 has been heat softened by ultrasonic vibratory energy, the material of the suture retainer is pliable and is plastically deformed by the force applied against the suture retainer by the anvil 90 and horn 92.

In addition to the anvil 90 and horn 92, the apparatus for transmitting ultrasonic vibratory energy to the suture retainer 34 includes a generator (not shown) which changes standard electrical power into electrical energy at the desired ultrasonic frequency. A transducer (not shown) changes the electrical energy into low amplitude mechanical motion or vibration. These vibrations are transmitted to a booster which is used to increase or decrease the amplitude of the vibrations. The vibrations are then transmitted to the horn 92.

The ultrasonic vibratory energy transmitted to the suture retainer 34 from the horn 92 is converted into heat energy. When this occurs, the temperature of the material forming the suture retainer 34 increases. The heat tends to concentrate at a boundary between the suture 32 and the suture retainer 34. Thus, the heat tends to concentrate in the areas where the suture 32 engages the grooves 80 and 82 and the passage 76 (FIG. 2).

As the temperature of the suture retainer 34 increases, the material of the suture retainer is heated into the transition temperature range and softens. However, the material of the suture retainer 34 does not melt and become liquid. As the material of the suture retainer 34 softens, the forces 96 and 98 (FIG. 3) applied against the suture retainer cause the material of the suture retainer to (flow or ooze around and engage the suture 32.

As the ultrasonic vibratory energy is effective to heat soften the material of the suture retainer 34, the grooves 80 and 82 close, that is, collapse. As the grooves 80 and 82 close, the central passage 76 also closes. As the grooves 80 and 82 and central passage 76 close, the softened material of the suture retainer 34 moves into engagement with the suture (FIG. 3).

The viscous material of the suture retainer 34 engages the suture 32 and bonds to the suture without significant deformation of the suture. The materials of the suture 32 and suture retainer 34 should be chemically compatible so that a molecular bond can be established between the suture retainer and the suture. Like materials, that is materials having chemical properties which are the same or very similar will usually bond together. However, dissimilar materials may bond if their melt temperatures are reasonably close and they are of like molecular structure. Generally speaking, amorphous polymers are readily bonded to each other.

The suture retainer 34 is formed separately from the suture 32. As the material of the suture retainer 34 bonds to the suture 32, the suture retainer 34 becomes fixedly connected to the suture.

If desired, heat may be transmitted directly to the suture retainer 34 during the transmission of ultrasonic vibratory energy to the suture retainer. The heat may be transmitted from a heating element disposed in the anvil 90 and/or the horn 92. Alternatively, a separate member could be utilized to transmit heat to the suture retainer 34.

In the embodiment of the invention illustrated in FIGS. 1-3, the anvil 90 and horn 92 have a configuration which corresponds to the arcuate configuration of the spherical outer side surface 84 (FIG. 2) of the suture retainer 34. The anvil 90 and horn 92 are configured so as to engage the material of the suture retainer 34 and to be spaced from the suture 32. This is to prevent excessive heating of the material of the suture 32 by the direct application of ultrasonic vibratory energy to the suture.

Embodiment of FIG. 4

In the embodiment of the invention illustrated in FIGS. 1-3, sections 38 and 40 of the suture 32 are wrapped around portions 52 and 54 of the suture retainer 34. In the embodiment of the invention illustrated in FIG. 4, a single section of the suture extends straight through a passage in the suture retainer. Since the embodiment of the invention illustrated in FIG. 4 is generally similar to the embodiment of the invention illustrated in FIGS. 1-3, similar terminology will be utilized to designate similar components. It should be understood that one or more of the features of any of the various embodiments of the invention disclosed herein may be used with the embodiment of the invention illustrated in FIG. 4.

In the embodiment of the invention illustrated in FIG. 4, a suture 112 is inserted through upper and lower (as viewed in FIG. 4) layers 114 and 116 of human body tissue in a sterile operating room environment. A first or inner end portion 118 of the suture 112 is connected with a suture anchor 120. The suture anchor 120 could have any desired construction, including the construction disclosed in U.S. Pat. Nos. 5,584,862; 5,549,631; and/or 5,527,343. However, the illustrated embodiment of the suture anchor 120 is a circular disc or button having a pair of central openings around which the end portion 118 of the suture 112 is tied.

The suture 112 extends straight through the lower layer 116 and upper layer 114 of body tissue. The two layers of body tissue are disposed in linear apposition with each other and are compressed between the suture anchor 120 and a suture retainer 124. The upper and lower layers 114 and 116 of body tissue are compressed by force applied against the body tissue by the suture retainer 124 and suture anchor 120. By having the layers 114 and 116 of body tissue approximated with each other and by pressing the layers of tissue together, healing of the tissue is promoted.

Although the layers 114 and 116 are layers of soft body tissue, the suture 112, suture anchor 120, and suture retainer 124 could be used with hard body tissue in the manner disclosed in U.S. Pat. No. 5,921,986. Alternatively, the suture 112, suture anchor 120, and suture retainer 124 could be used to connect soft body tissue with hard body tissue.

The suture retainer 124 has a spherical configuration and is formed separately from the suture 112. A cylindrical passage 126 extends axially through the suture retainer 124. Although the suture 112 extends straight through the passage 126 in the suture retainer 124, bends and/or loops could be formed in the suture 112 around the suture retainer 124.

The suture retainer 124 is formed of one piece of spherical polymeric material having a relatively low coefficient of friction. The suture retainer 124 may be formed of many different materials. However, it is believed that it may be preferred to form the suture retainer 124 of a biodegradable polymer such as polycaperlactone or polyhydroxyalkanoate. It is contemplated that other biodegradable or bioerodible polymers could be utilized if desired. It is believed that it may be preferred to form the suture retainer 124 of an amorphous thermoplastic material.

The suture 112 may be a monofilament or may be formed of a plurality of interconnected filaments. The suture 112 may be biodegradable or non-biodegradable. It is believed that it will be preferred to form the suture 112 of the same material as the suture retainer 124. However, the suture 112 could be formed of a material which is different than the material of the suture retainer. The suture 112 may be formed of an amorphous thermoplastic having chemical properties which are the same or similar to the chemical properties of the suture retainer 124. For example, both the suture retainer 124 and the suture 112 may be formed of the same biodegradable polymer, such as polycaperlactone or polyhydroxyalkanoate.

The suture 112 is tensioned with a force which is a function of the size and strength of the suture. In addition, the suture retainer 124 is pressed against the upper layer 114 of body tissue with a force which is a function of the size and strength of the suture 112. Although the suture retainer 124 is disposed in direct engagement with and is pressed against an outer side surface of the upper layer 114 of body tissue, a force distribution member or button could be positioned between the suture retainer and the upper layer 114 of body tissue.

The suture 112 is tensioned by a force application assembly 130 which is connected with a second or outer end portion 132 of the suture 112. The force application assembly 130 includes a transducer or load cell 134 which provides an output signal indicative of a force, indicated schematically at 136 in FIG. 4, which is applied to the second or outer end portion 132 of the suture 112. The force 136 has a magnitude which is a function of the size and strength of the suture 112 and the characteristics of the body tissue with which the suture is associated, that is, the upper layer 114 and lower layer 116 of body tissue.

The suture retainer 124 is pressed against the body tissue with a force which is also a function of the strength and size of the suture 112. A force application member 140 is used to apply force against the suture retainer 124. The force application member 140 has a cylindrical opening 142 which extends through the force application member.

The suture 112 extends through the opening 142 in the force application member 140. A slot may be formed in the force application member 140 to enable the suture to be moved into the opening 142. Alternatively, the suture 112 could be inserted through the opening 142 before the end portion of the suture is connected with the force application assembly 130.

Forces, indicated schematically at 146 and 148 in FIG. 4, are applied against opposite end portions 150 and 152 of the force application member 140 to press the suture retainer 124 against the upper layer 114 of body tissue or against a force transmitting member disposed between the suture retainer 124 and the upper layer 114 of body tissue. The combined force indicated schematically by the arrows 146 and 148 in FIG. 4, is a function of the size and strength of the suture 112 and the characteristics of the layers 114 and 116 of body tissue. It is contemplated that the combined forces 146 and 148 may be equal to the force 136. Alternatively, the summation of the forces 146 and 148 could exceed the force 136 or be less than the force 136.

The suture retainer 124 slides downward (as viewed in FIG. 4) along the suture 112 under the influence of the force application member 140. At this time, the suture 112 is tensioned by the force application assembly 130 so that the portion of the suture extending between the suture anchor 120 and the force application assembly 130 is straight, as illustrated in FIG. 4. However, at this time, the force which is applied to the outer end portion 132 by the force transmitting assembly may be substantially less than the force which is indicated schematically by the arrow 136 in FIG. 4.

After the suture retainer 124 has been moved along the suture 112 to the position illustrated in FIG. 4, the force applied against the suture retainer by the force application member 140 is increased. At the same time, the force applied to the outer end portion 132 of the suture 112 by the force application assembly 130 is increased. The force applied against the suture retainer by the force application member 140 is increased until the force, indicated schematically by the arrows 146 and 148 in FIG. 4, is equal to a predetermined force which is a function of the strength of the suture 112 and the characteristics of the layers 114 and 116 of body tissue. At the same time, the force applied to the outer end portion 132 of the suture 112 by the force application assembly 130 is increased to the force indicated schematically by the arrow 136 in FIG. 4. As was previously mentioned, the force indicated by the arrow 136 is a predetermined function of the strength of the suture 112 and the characteristics of the layers 114 and 116 of body tissue.

While the suture 112 is being pulled straight under the influence of tension in the suture due to the force 136 and while the suture retainer 124 is being pressed against the upper layer 114 of body tissue or against a suitable force distribution member, the suture retainer 124 is heated to grip the suture 112. In accordance with one of the features of the invention, the suture retainer 124 is heated by the application of ultrasonic vibratory energy to the suture retainer. The ultrasonic vibratory energy is converted into heat by the molecules of the suture retainer 124. Thus, the mechanical ultrasonic vibrations applied against the suture retainer 124 cause molecular vibration of the material of the suture retainer and a heating of the suture retainer.

When a portion of the material forming the suture retainer 124 has been heated into its transition temperature range, the application of ultrasonic vibratory energy to the suture retainer 124 is interrupted. Heating the material forming the suture retainer 124 causes the material to lose its rigidity and soften. The material of the suture retainer 124 is not melted and does not become liquid by being heated into its transition temperature range. The softened material of the suture retainer 124 bonds to the suture 112 without significant deformation of the suture.

To apply ultrasonic vibratory energy to the suture retainer 124, a support member or anvil 160 engages one side, that is the left side as viewed in FIG. 4, of the suture retainer 124. At the same time, a horn or acoustic tool is pressed against the opposite or right side (as viewed in FIG. 4) of the suture retainer 124.

The anvil 160 and horn 162 are pressed against opposite sides of the suture retainer 124 with predetermined forces, indicated schematically by arrows 164 and 166 in FIG. 4. After the suture retainer 124 has been firmly clamped between the anvil 160 and horn 162, the horn is vibrated with an ultrasonic frequency, that is with a frequency which is greater than 20 kilohertz. It is contemplated that the horn 162 may be vibrated at a selected frequency within a range of ultrasonic frequencies which extends between 20 kilohertz and 70 kilohertz. Although the particular ultrasonic frequency with which the horn 162 is vibrated will vary depending upon the composition and construction of the suture retainer 124, it is believed that it may be preferred to vibrate the horn 162 with a frequency which is close to or greater than 70 kilohertz.

The mechanical vibrations applied to the suture retainer 124 by the horn 162 are effective to heat a portion of the material of the suture retainer 124 into the transition temperature range. The heat tends to concentrate on the portion of the suture retainer 124 adjacent to the passage 126 and the suture 112. When the material of the suture retainer 124 adjacent to the suture 112 has been heated into its transition temperature range, the application of ultrasonic vibratory energy to the suture retainer 124 is interrupted. The forces 164 and 166 are effective to close or collapse the passage 126 and to press the softened material of the suture retainer 124 against the suture 112.

Although the application of ultrasonic vibratory energy to the suture retainer 124 is interrupted, the anvil 160 and horn 162 continue to apply the forces 164 and 166 against the softened material of the suture retainer. If desired, the forces 164 and 166 may be increased when the application of ultrasonic vibratory energy to the suture retainer 124 by the horn 162 is interrupted. The forces 164 and 166 firmly press the heat-softened material of the suture retainer 124 into the passage 126 to collapse the passage. The heat softened material of the suture retainer 124 is plastically deformed and pressed against the suture 112 by the forces 164 and 166 applied against the suture retainer by the anvil 160 and horn 162.

The forces 164 and 166 are maintained for a sufficient period of time to enable the material of the suture retainer 124 to bond to the suture 112 without significant deformation of the suture. Once this bonding has been achieved, application of the forces 164 and 166 is interrupted and the anvil 160 and horn 162 are withdrawn. The force application member 140 may then be disengaged from the suture retainer and the force application assembly 130 disconnected from the outer end portion 132 of the suture 112.

When the layers 114 and 116 of body tissue are to be interconnected with the suture 112, suture anchor 120 and suture retainer 124, the upper layer 114 is moved into apposition with the lower layer 116 of body tissue. The suture 112 is then connected with the suture anchor 120 and is inserted through the layers 114 and 116 of body tissue with a suitable needle. The outer end portion 132 of the suture 112 is then inserted through the passage 126.

The suture retainer 124 is then moved along the suture 112 into engagement with the upper layer 114 of body tissue. The force application member 140 is utilized to transmit the forces 146 and 148 to the suture retainer 124 to press the suture retainer against the upper layer 114 of body tissue. This results in the two layers 114 and 116 of body tissue being pressed firmly together between the suture retainer 124 and suture anchor 112. The forces 146 and 148 are transmitted to the suture retainer 124 through the force application member 140. The suture 112 is tensioned with a force 136 by the force application assembly 130.

The anvil 160 and horn 162 then compress the suture retainer 124 under the influence of the forces 164 and 166. Ultrasonic vibratory energy is transmitted to the suture retainer. Upon heating and softening of at least a portion of the material of the suture retainer 124, the transmission of ultrasonic energy to the suture retainer is interrupted and a bonding of the material of the suture retainer to the suture 112 occurs. After the suture retainer 124 has firmly gripped the suture 112, the application of the forces 164 and 166 is interrupted.

In the foregoing explanation of the manner in which the layers 114 and 116 of body tissue are secured by the use of the suture 112, suture anchor 120 and suture retainer 124, the suture retainer has been heated by only the application of ultrasonic vibratory energy to the suture retainer. However, it is contemplated that heat energy could be transmitted directly to the suture retainer along with the ultrasonic vibratory energy. If this was to be done, a heating element could be provided in the anvil 160 and/or horn 162. If desired, a separate heating element could engage the suture retainer to transmit the heat to the suture retainer separately from the anvil 160 and horn 162.

It is believed that it probably will be preferred to have the anvil 160 and horn 162 engage the suture retainer 124 at locations spaced from the suture 112 to prevent excessive heating of the material of the suture. If desired, protective collars could be provided around the suture 112 at opposite ends of the passage 126.

Figure 5:
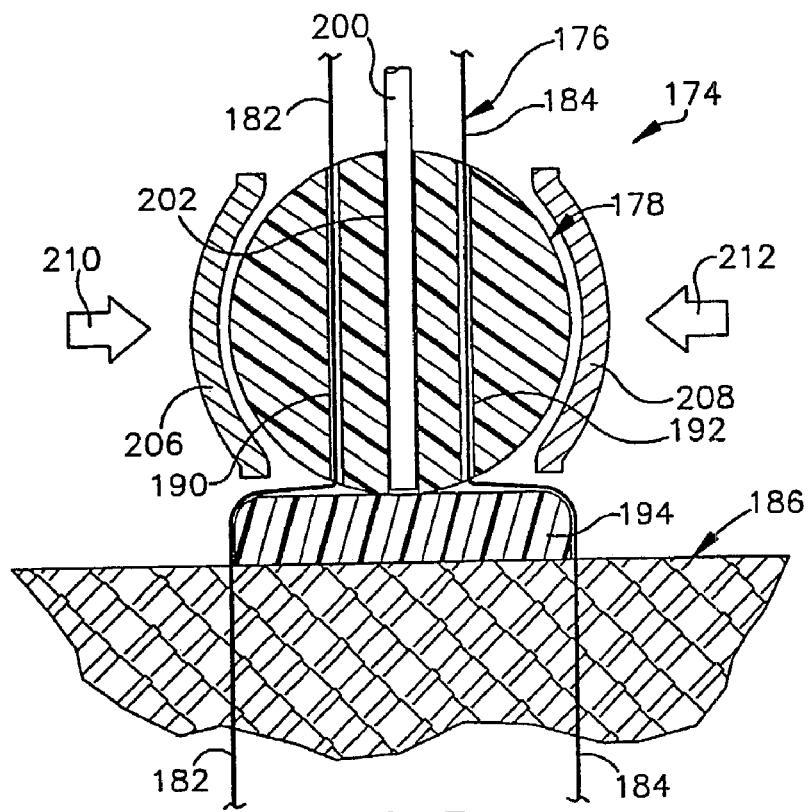
FIG. 5 is a schematic fragmentary sectional view of another embodiment of the invention and illustrating the manner in a vibration applicator member engages a suture retainer which is being pressed against body tissue with a predetermined force while an associated suture is tensioned with a predetermined force.

Embodiment of FIG. 5

In the embodiment of the invention illustrated in FIG. 4, a single section of the suture 112 extends through a single passage 126 in the suture retainer 124. In addition, in the embodiment of the invention illustrated in FIG. 4, ultrasonic vibratory energy is applied to the suture retainer 124 by the horn 162 which also applies a compressive force 166 against the suture retainer. In the embodiment of the invention illustrated in FIG. 5, a plurality of sections of the suture extend through a plurality of passages in the suture retainer. In addition, ultrasonic vibratory energy is applied to the suture retainer by a member which is separate from the members which apply force against opposite sides of the suture retainer. Since the suture retainer of the embodiments of the invention illustrated in FIGS. 1-4 are similar to the embodiment of the suture retainer illustrated in FIG. 5, similar terminology will be utilized to designate similar components. It should be understood that one or more of the features of any of the embodiments of the invention disclosed herein may be used with the embodiment of the invention illustrated in FIG. 5.

A tissue securing system 174 is used in a sterile, operating room environment and includes a suture 176 and a suture retainer 178. The suture 176 has left and right sections 182 and 184 which extend into human body tissue 186. The body tissue 186 may include a plurality of layers which are approximated in linear apposition with each other in the manner previously described in conjunction with the embodiment of the invention illustrated in FIG. 1.

Although the suture 176 has been illustrated in FIG. 5 in association with soft body tissue 186, it is contemplated that the suture 176 could be associated with hard or hard and soft body tissue. In the embodiment of the invention illustrated in FIG. 5, the suture sections 182 and 184 are interconnected by a connector section which engages the body tissue in the manner illustrated schematically in FIG. 1. However, it should also be understood that the suture 176 could be associated with a suture anchor, similar to the suture anchor 120 of FIG. 4, if desired. Rather than being disposed in engagement with an outer side surface of a layer of body tissue, the suture anchor could be embedded in the body tissue.

The suture retainer 178 has a spherical configuration and is formed separately from the suture 176. A pair of parallel passages 190 and 192 extend through the suture retainer 178 at locations offset to opposite sides of a central or polar axis of the suture retainer. A force transmitting member 194 is provided between the suture retainer 178 and the body tissue 186.

The sections 182 and 184 of the suture 176 press against opposite sides of the force transmitting member 194. If desired, the force transmitting member 194 could be provided with grooves or passages to receive the sections 182 and 184 of the suture 176. The force transmitting member 194 could be integrally formed as one piece with the suture retainer 178. Both the force transmitting member 194 and suture retainer 178 are formed separately from the suture 176.

In accordance with a feature of this embodiment of the invention, ultrasonic vibratory energy is applied to the suture retainer 178 by a horn or acoustic tool 200. The horn 200 extends into a cylindrical passage 202 formed in the suture retainer 178. The passage 202 extends parallel to and is disposed midway between the passages 190 and 192 which receive the sections 182 and 184 of the suture 176.

In the embodiment of the invention illustrated in FIG. 5, the horn 200 has a generally cylindrical configuration which corresponds to the cylindrical configuration of the passage 202. However, the horn 200 and passage 202 could have different configurations if desired. For example, the horn 200 and passage 202 could have frustroconical configurations.

A pair of force application members or anvils 206 and 208 are pressed against opposite sides of the suture retainer 178 with predetermined forces, indicated schematically by arrows 210 and 212 in FIG. 5. The anvils 206 and 208 have arcuate configurations which correspond to the arcuate configuration of the suture retainer 178. Of course, the anvils 206 and 208 could have a different configuration if desired.

When the tissue securing system 174 is to be utilized to secure the body tissue 186, the suture 176 is positioned relative to the body tissue in the manner illustrated schematically in FIG. 1. However, if desired, a separate anchor, similar to the anchor 120 of FIG. 4, could be connected with an end portion of each of the sections 182 and 184 of the suture 176. If this was done, the sections 182 and 184 of the suture 176 could be separate from each other and interconnected by the body tissue 176 and suture retainer 178. Thus, two separate segments of suture, that is the sections 182 and 184, would be interconnected by a single suture retainer.

After the suture 176 has been positioned relative to the body tissue, the upper (as viewed in FIG. 5) end portions of the sections 182 and 184 of the suture 176 are inserted through the passages 190 and 192. The force distribution member 194 is positioned between the suture retainer 178 and the body tissue 176. The sections 182 and 184 of the suture are then tensioned with a predetermined force. The suture retainer 178 is moved along the sections 182 and 184 of the suture 176 into engagement with the force distribution member 194.

When the suture retainer 178 has been moved along the sections 182 and 184 of the suture 176 into engagement with the force distribution member 194, a predetermined force is applied against suture retainer 178, in the manner similar to that indicated schematically in FIG. 4, to press the force transmitting member 194 against the body tissue 186 with a predetermined force. At the same time, the sections 182 and 184 of the suture 176 are tensioned with a predetermined force. If the sections 182 and 184 are formed by a single piece of suture 176, in the manner illustrated schematically in FIG. 1, a connector section of the suture is pulled against the body tissue to compress the body tissue between the suture retainer 178 and the connector section of the suture. Alternatively, if separate suture anchors are connected with the sections 182 and 184 of the suture 176, the two spaced apart suture anchors are pulled against the body tissue to compress the body tissue 186 between the suture anchors and the suture retainer 178.

While the suture 176 is being tensioned with a predetermined force and while the suture retainer 178 is being pressed against the force distribution member 194 with a predetermined force, the suture retainer 178 is deformed to grip the sections 182 and 184 of the suture 176. This deformation of the suture retainer 178 results in a firm gripping of the sections 182 and 184 of the suture 176 to maintain a desired tension force in the suture and to maintain a desired compression force against the body tissue 186.

To deform the suture retainer 178 to grip the suture 176, the anvils 206 and 208 are pressed against opposite sides of the suture retainer with a predetermined force, as indicated schematically by the arrows 210 and 210 in FIG. 5. The horn 200 is then vibrated with an ultrasonic frequency to transmit ultrasonic vibratory energy to the suture retainer 178. It is contemplated that the horn 200 may be vibrated at a frequency of between 20 and 70 kilohertz. It is believed that it may be preferred to vibrate the horn 200 at a frequency which is close to or greater than 70 kilohertz.

Vibration of the horn 200 at ultrasonic frequencies transmits mechanical vibrational energy form the horn 200 to the suture retainer 178. This ultrasonic vibrational energy is converted into heat energy and results in a heating of the suture retainer 178. The heat in the suture retainer tends to be concentrated in the material of the suture retainer at locations adjacent to the passages 190 and 192. When the material of the suture retainer 178 adjacent to the passages 190 and 192 has been heated into a transition temperature range for the material, the material of the suture retainer becomes soft and relatively pliable. However, the material of the suture retainer 178 does not melt and become liquid. The transmission of ultrasonic vibratory energy from the horn 200 to the suture retainer 178 is then interrupted.

The anvils 206 and 208 continue to be pressed against the suture retainer 178 with the forces indicated schematically by the arrows 210 and 212 in FIG. 5. If desired, the force applied against the suture retainer 178 may be increased upon interruption of the transmission of ultrasonic vibratory energy to the suture retainer. The force 210 and 212 applied by the anvils 206 and 208 against the suture retainer 178 is effective to plastically deform the heat softened material of the suture retainer. The force applied by the anvils 206 and 208 collapses the passages 190 and 192 and presses the softened material of the suture retainer 178 against the sections 182 and 184 of the suture 176.

The suture retainer 178 and suture 176 may be formed of many different materials. However, it is believed that it will be preferred to form the suture retainer 178 and the suture 176 of a biodegradable polymer. The biodegradable polymer may advantageously be an amorphous thermoplastic. Bonding of the material of the suture retainer 178 with the material of the suture 176 is promoted by forming the suture retainer and suture of the same material. However, the suture retainer 178 and suture 176 could be formed of different materials having similar chemical properties and which are compatible with each other.

In the embodiment of the invention illustrated in FIG. 5, the material of the suture retainer 178 is heated by the application of ultrasonic vibratory energy to the suture retainer by the horn 200. However, it is contemplated that heat energy could be directly transmitted to the suture retainer 178 during the transmission of ultrasonic vibratory energy to the suture retainer if desired. To effect the transmission of heat energy to the suture retainer 178, heating elements could be provided in the anvils 206 and 208.

Figure 6:
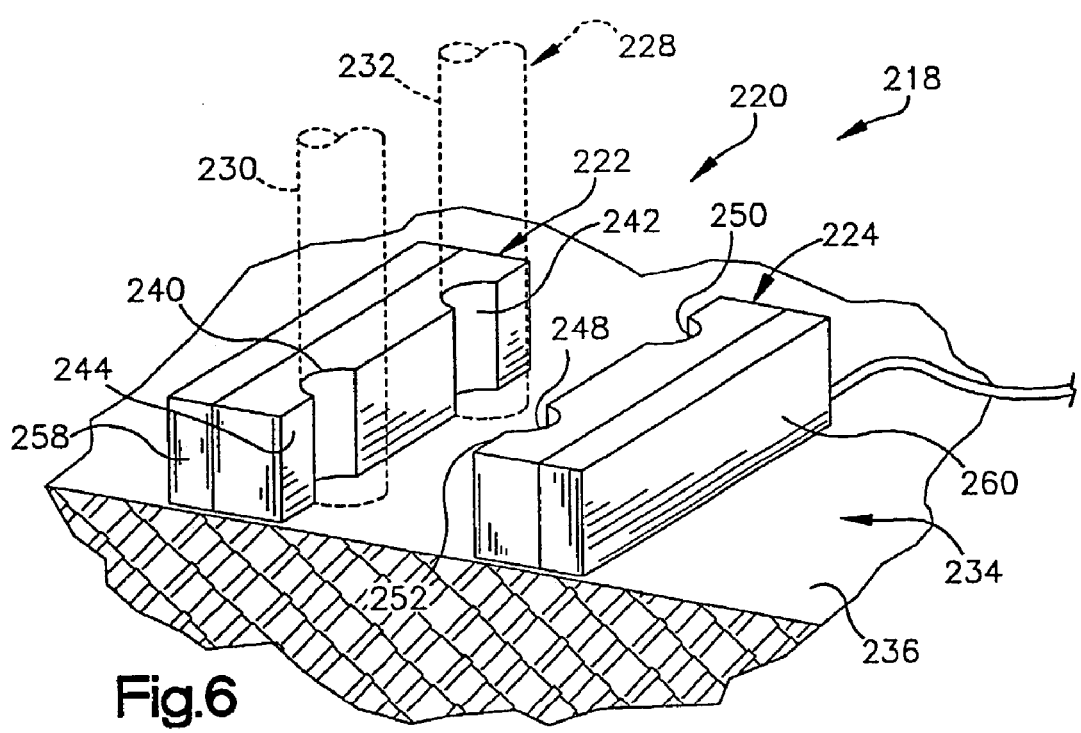
FIG. 6 is a schematic fragmentary pictorial illustration of another embodiment of the invention and depicting the construction of sections of a suture retainer and the relationship of the sections of the suture retainer to apparatus for applying ultrasonic vibratory energy to the suture retainer.

Embodiment of FIG. 6

In the embodiment of the invention illustrated in FIGS. 1-5, the suture retainer has a generally spherical configuration and is formed as one piece. In the embodiment of the invention illustrated in FIG. 6, the suture retainer is formed as two pieces. Since the suture retainer of FIG. 6 is similar to the suture retainers of FIGS. 1-5, similar terminology will be utilized to identify similar components. It should be understood that one or more features of other embodiments of the invention disclosed herein could be used with the embodiment of the invention illustrated in FIG. 6.

A tissue securing system 218 (FIG. 6) is used in a sterile, operating room environment and includes a suture retainer 220 and suture 228. The suture retainer 220 includes two sections, that is, a left (as viewed in FIG. 6) section 222 and a right section 224. The left and right sections 222 and 224 of the suture retainer 220 are formed separately from each other. However, it is contemplated that the two sections 222 and 224 could be interconnected by a flexible connector section. The flexible connector section may be formed as one piece with the left section 222 and the right section 224 of the suture retainer 220.

A suture 228 includes sections 230 and 232 which are formed separately from the sections 222 and 224 of the suture retainer 220. The suture 228 is positioned relative to human body tissue 234 with the sections 230 and 232 extending away from an outer side surface 236 of the body tissue. The suture 228 may be connected with the body tissue 234 in the same manner as illustrated schematically in FIG. 1 if desired.

Although the suture 228 has been illustrated schematically in FIG. 6 in association with soft body tissue 234, it is contemplated that the suture could be associated with hard body tissue or with both hard and soft body tissue. It is also contemplated that the suture 228 could extend through a suture anchor which is disposed in engagement with a surface of the body tissue or embedded in the body tissue.

The left section 222 of the suture retainer 220 has a generally rectangular configuration. The left section 222 of the suture retainer 220 includes a pair of parallel grooves 240 and 242. The grooves 240 and 242 extend inward, that is, toward the left as viewed in FIG. 6, from a flat major side surface 244 of the left section 222 of the suture retainer 220. The grooves 240 and 242 are each formed as a portion of a cylinder.

Each of the grooves 240 and 242 has an extent which is slightly less than one-half of the circumferential extent of a cylinder. The radius of the grooves 240 and 242 is the same as the radius of the suture sections 230 and 232. Since the grooves 240 and 242 have side surfaces which are formed as a portion of a cylinder and have an extent which is slightly less than one-half of the diameter of the cylinder, less than half of each of the suture sections 230 and 232 is disposed in a groove 240 and 242.

The right section 224 of the suture retainer 222 has a configuration which is the same as the configuration of the left section 222. Thus, the right section 224 of the suture retainer 220 includes a pair of grooves 248 and 250. The grooves 248 and 250 extend inward, that is toward the right, as viewed in FIG. 6, from a flat major side surface 252 of the right section 224 of the suture retainer 220.

The grooves 248 and 250 are each formed as a portion of a cylinder. However, the grooves 248 and 250 have an extent which is slightly less than one-half the circumferential extent of the cylinder. The grooves 248 and 250 have a radius which is the same as the radius of the suture sections 230 and 232.

In one specific embodiment of the invention, the identical left and right sections 222 and 224 had a rectangular configuration. The major side surfaces 244 and 252 had a length, as measured transversely to the grooves 240, 242, 248 and 250, of approximately 0.236 inches. The major side surfaces 244 and 252 had a width, as measured parallel to the grooves 240, 242, 248 and 250, of approximately 0.119 inches. The left and right sections 222 and 224 had a thickness, as measured perpendicular to the major side surfaces 244 and 252, of approximately 0.055 inches. The grooves 240, 242, 248, and 250 had a radius of approximately 0.046 inches. The depths of the grooves 240, 242, 248 and 250 was approximately 0.005 inches less than the radius of the grooves or about 0.041 inches.

It should be understood that the foregoing dimensions for one specific preferred embodiment of the suture retainer 222 have been set forth herein for purposes of clarity of description. It is contemplated that the sections 222 and 224 of the suture retainer 220 will be constructed with dimensions which are substantially different from the specific dimensions which have been set forth herein.

The two sections 222 and 224 of the suture retainer 220 may be formed of many different materials. However, it is believed that it will be preferred to form the sections 222 and 224 of the suture retainer 220 of a biodegradable polymer. The two sections 222 and 224 of the suture retainer 220 may be formed of an amorphous thermoplastic material. The suture 228 and the suture retainer 220 may be formed of any of the materials previously mentioned herein or other materials. The suture 228 and the suture retainer 220 may be formed from the same material or from different materials having the same or similar chemical properties which are compatible with each other.

When the suture 228 and suture retainer 220 are to be used to secure the human body tissue 234, the suture 228 is positioned relative to the body tissue. The suture 228 may be positioned relative to the body tissue in the manner illustrated schematically in FIG. 1. Alternatively, the suture 228 may be connected with one or more suture anchors. A predetermined tension force is then applied to the sections 230 and 232 of the suture.

The two sections 222 and 224 of the suture retainer 220 are positioned in engagement with the sections 230 and 232 of the suture 228. The suture retainer 220 is pressed against the body tissue 234 with a predetermined force. This results in the body tissue being pressed between the suture retainer 220 and the portion of the suture connected with the body tissue 234. A force distribution member could be provided between the suture retainer 220 and body tissue 234 if desired.

The left section 222 of the suture retainer 220 is positioned in abutting engagement with the sections 230 and 232 of the suture 228 and with the body tissue 234 in the manner illustrated schematically in FIG. 6. The right section 224 of the suture retainer 220 is moved into engagement with the sections 230 and 232 of the suture 228 and is also pressed against the body tissue 234. At this time, the major side surface 252 on the right section 224 of the suture retainer 220 is spaced from and extends parallel to the major side surface 244 on the right section 222 of the suture retainer 220. The two sections 222 and 224 of the suture retainer 220 are spaced apart by a distance which is a function of the extent by which the diameters of the suture sections 230 and 232 exceed the combined depth of the grooves 240 and 248 and the combined depth of the grooves 242 and 250 in the sections 222 and 224 of the suture retainer 220.

In the specific example for which dimensions have been set forth herein, the major side surface 244 of the left section 222 of the suture retainer 220 is spaced 0.010 inches from the major side surface 252 of the right section 224 of the suture retainer 220. It should be understood that a different spacing could be provided between the major side surfaces 244 and 252 of the suture sections 222 and 224 when the grooves 240 and 242 in the suture section 222 are in engagement with the suture sections 230 and 232 and the grooves 248 and 250 in the right suture section 224 are in engagement with the suture sections 230 and 232.

In order to bond the sections 222 and 224 of the suture retainer 220 to each other and to the sections 230 and 232 of the suture 228, ultrasonic vibratory energy is transmitted to the suture retainer 220. At this time, the suture retainer 228 is pressed against the body tissue 234 with a predetermined force and the sections 230 and 232 of the suture 228 are tensioned with a predetermined force.

To effect the transmission of ultrasonic vibratory energy to the sections 222 and 224 of the suture retainer 220, an anvil 258 is moved into engagement with the left section 222 of the suture retainer 220. A horn or acoustic tool 260 is moved into engagement with the right section 224 of the suture retainer 220. The anvil 258 and horn 260 are pressed against the sections 222 and 224 of the suture retainer 220 with a predetermined force to firmly press the sections of the suture retainer against the sections 230 and 232 of the suture 228.

While the anvil 258 and horn 260 are being pressed against the suture retainer sections 222 and 224 with a predetermined force, ultrasonic vibrations are transmitted from the horn 260 to the suture retainer 220. The ultrasonic vibrations transmitted from the horn 260 to the suture retainer 220 have a frequency in excess of 20 kilohertz. The ultrasonic vibrations transmitted to suture retainer 220 by the horn 260 may have a frequency of between 20 kilohertz and 70 kilohertz. It is believed that it may be preferred to transmit ultrasonic vibrations having a frequency close to or greater than 70 kilohertz to the suture retainer 220 from the horn 260.

The ultrasonic vibrations transmitted to the suture retainer 220 create frictional heat and cause portions of the material of the suture retainer 220 to be heated into the transition temperature range for the material. As the material of the suture retainer 220 is heated into its transition temperature range, the material loses some of its rigidity and softens. The material of the suture retainer 220 does not melt and become liquid. The heat in the suture retainer 220 will tend to be concentrated adjacent to the grooves 240, 242, 248 and 250 and adjacent to the major side surfaces 244 and 252.

As the material of the suture retainer 220 is heated and softened by the ultrasonic vibratory energy, the sections 222 and 224 of the suture retainer 220 are pressed together by force applied against the sections of the suture retainer by the anvil 258 and horn 260. As this occurs, the material of the sections 222 and 224 of the suture retainer 220 is plastically deformed and pressed against the sections 230 and 232 of the suture 228 at the grooves 240, 242, 248 and 250 in the suture retainer. At the same time, at least portions of the major side surfaces 248 and 252 on the sections 222 and 224 of the suture retainer 220 will move into engagement with each other.

When this has occurred, the transmission of ultrasonic energy to the suture retainer 228 is interrupted. However, the force applied against the sections 222 and 224 is maintained. It is believed that it may be desired to increase the force applied against the sections 222 and 224 of the suture retainer 220 by the anvil 258 and horn 260 as the application of ultrasonic vibratory energy to the suture retainer 220 is interrupted.

While the clamping force applied by the anvil 258 and horn 260 is maintained, the left and right sections 222 and 224 of the suture retainer 220 bond to each other. In addition, the left and right sections 222 and 224 of the suture retainer 220 bond to the sections 230 and 232 of the suture 228. This results in the suture 228 being firmly gripped by the sections of the suture retainer 220. The sections 222 and 224 of the suture retainer 220 bond to the suture 228 without significant deformation of the suture.

The left and right sections 222 and 224 of the suture retainer 220 bond to each other at a joint formed between the surfaces 244 and 252 of the sections of the suture retainer. This results in a bonding of the sections 222 and 224 of the suture retainer 220 at locations offset to both sides of the suture 228 and at locations offset to both sides of the suture 230. The material of the sections 222 and 224 of the suture retainer 220 defining the grooves 240, 242, 248 and 250 bond to the outer side surfaces of the sections 230 and 232 of the suture 228.

Although it is preferred to heat the sections 222 and 224 of the suture retainer 220 with ultrasonic vibratory energy in the manner previously explained, it is contemplated that heat energy could be directly transmitted to the suture retainer if desired during the transmission of ultrasonic vibratory energy to the suture retainer. The heat energy could be transmitted to the suture retainer 220 from heating coils in the anvil 258 and/or horn 260. If desired, a separate heat application member could be provided.

The sections 222 and 224 of the suture retainer 220 prevent direct engagement of the anvil 258 and horn 260 with the suture 228. This prevents excessive heating of the suture 228.

Embodiment of FIGS. 7 and 8

In the embodiment of the invention illustrated in FIG. 6, the suture retainer 220 is formed in two sections 222 and 224. In the embodiment of the invention illustrated in FIGS. 7 and 8, the suture retainer is formed as one piece having passages for receiving the sections of the suture. Since the embodiment of the invention illustrated in FIGS. 7 and 8 is generally similar to the embodiment of the invention illustrated in FIGS. 1-6, similar terminology will be utilized to identify similar components. It should be understood that one or more of the features of the other embodiments of the invention illustrated herein could be utilized in association with the embodiment of the invention illustrated in FIGS. 7 and 8.

A tissue securing system 268 is used in a sterile, operating room environment and includes a suture retainer 270 and a suture 280. The suture retainer 270 is integrally formed as one piece and has a cylindrical configuration. A pair of cylindrical passages 272 and 274 (FIG. 7) extend diametrically through the suture retainer 270. Of course, the suture retainer 270 and passages 272 and 274 could have a different configuration if desired. For example, the suture retainer 270 could have an oval or a polygonal configuration.

Left and right sections 276 and 278 of a suture 280 extend through the passages 272 and 274. The suture sections 276 and 278 are connected with layers of human body tissue (not shown) in the same manner as has been illustrated schematically in FIG. 1. However, the suture sections 276 and 278 could be connected with a suture anchor embedded in the body tissue. Alternatively, each of the sections 276 and 278 of the suture 280 could be connected with a separate suture anchor, in much the same manner as in which the one section of the suture 112 of FIG. 4 is connected with the suture anchor 120.

It is contemplated that the suture retainer 270 and suture 280 could be used in association with hard body tissue, soft body tissue, or hard and soft body tissue. The suture retainer 270 and suture 280 may be used with body tissue in any one of the ways previously described herein. Of course, the suture retainer and suture may be used with body tissue in other known ways if desired.

The suture retainer 270 may be formed of many different materials. However, It is believed that it will be preferred to form the suture retainer 270 of a biodegradable polymer. It is believed that it may be preferred to form both the suture retainer 270 and the suture 280 of the same amorphous thermoplastic material. However, if desired, the suture 280 and suture retainer 270 could be formed of different materials which have the same or similar chemical properties and are compatible with each other. The suture 280 and/or the suture retainer 270 may be formed of either biodegradable or non-biodegradable materials.

In one specific embodiment of the invention, the cylindrical suture retainer 270 had a diameter of 0.119 inches. This particular suture retainer 270 had an axial extent of 0.236 inches. The passages 272 and 274 each had a diameter of 0.046 inches. If desired, the passages 272 and 274 could be formed with an oval configuration with parallel flat surfaces having a length of 0.030 inches extending between semicircular opposite end portions of the ovals.

It should be understood that the foregoing specific dimensions for embodiments of the suture retainer 270 have been set forth herein for purposes of clarity of description. It is contemplated that the suture retainer 270 can and will be formed with dimensions which are different than these specific dimensions. It is also contemplated that the suture retainer 270 will be constructed with a configuration which is different than the specific configuration illustrated herein. For example, the suture retainer 270 could have a prismatic configuration with the passages 272 and 274 extending between one corner portion and a side surface of the prism.

The suture 280 is positioned relative to body tissue in much the same manner as illustrated in FIG. 1. The sections 276 and 278 of the suture 280 are then inserted through the passages 272 and 274 (FIG. 7). While the suture 280 is tensioned, the suture retainer 270 is moved along the suture toward the body tissue. A predetermined force is transmitted from the suture retainer 270 to the body tissue while the sections 276 and 278 of the suture 280 are tensioned with a predetermined force in the manner previously described in conjunction with the embodiment of the invention illustrated in FIG. 4.

While the body tissue is compressed between the suture 280 and the suture retainer 270, ultrasonic vibratory energy is transmitted to the suture retainer 270. To transmit ultrasonic vibratory energy to the suture retainer 270, an anvil 286 (FIG. 8) and a horn or acoustic tool 288 are pressed against opposite sides of the suture retainer 270 with a predetermined force. The suture 280 is tensioned and the suture retainer 270 is pressed against body tissue with predetermined forces while the anvil 286 and horn 288 are pressed against the suture retainer.

The horn 288 is then vibrated at an ultrasonic frequency, that is, at a frequency greater than 20 kilohertz. The horn 280 may be vibrated at a frequency of between 20 and 70 kilohertz. It is believed that it may be preferred to vibrate the horn 288 at a frequency close to or greater than 70 kilohertz. As this occurs, vibratory mechanical energy at ultrasonic frequencies is transmitted from the horn 288 to the suture retainer 270.

The ultrasonic vibratory energy transmitted from the horn 288 to the suture retainer 270 is effective to heat the suture retainer. The heat tends to be concentrated in the portion of the suture retainer 270 adjacent to the sections 276 and 278 of the suture 280.

When the portion of the suture retainer 270 adjacent to the sections 276 and 278 of the suture 280 have been heated to a temperature in the transition temperature range for the material of the suture retainer 270, the application of ultrasonic vibratory energy to the suture retainer 270 by the horn 288 is interrupted. When material of the suture retainer 270 is heated into the transition temperature range, the material of the suture retainer becomes soft and pliable. Although the material of the suture retainer 270 does not melt and become liquid, the material of the suture retainer 270 is softened and loses its rigidity when it is heated into the transition temperature range.

The force applied against the suture retainer 270 is then maintained or increased. The force applied against the suture retainer 270 by the anvil 286 and horn 288 is effective to plastically deform the material of the suture retainer. As the heat softened material of the suture retainer 270 is plastically deformed by the anvil 286 and horn 288, the material of the suture retainer is firmly pressed against the sections 276 and 278 of the suture 280.

As the heated and softened material of the suture retainer 270 cools, the material of the suture retainer bonds to the suture 280. This results in the suture retainer 270 securely gripping the sections 276 and 278 of the suture 280. The suture 280 is not significantly deformed as the suture retainer 270 is heated and bonded to the suture. Therefore, the strength of the suture 280 is not significantly reduced.

In the foregoing description, the suture retainer 270 was heated by the application of ultrasonic vibratory energy to the suture retainer. It is contemplated that heat energy could be transmitted to the suture retainer 270 along with the ultrasonic vibratory energy. This could be accomplished in many different ways. For example, a heating element could be provided in the anvil 286 and/or horn 288. Alternatively, a separate heating element could be moved into contact with the suture retainer 270.

Embodiment of FIG. 9

In the embodiment of the invention illustrated in FIGS. 7 and 8, the suture 280 extends through passages 272 and 274 formed in the suture retainer 270. In the embodiment of the invention illustrated in FIG. 9, the suture is wrapped around a section of the suture retainer and is engaged by other sections of the suture retainer. Since the suture retainer of the embodiments of the invention illustrated in FIGS. 1-8 is similar to the suture retainer of the embodiment of the invention illustrated in FIG. 9, similar terminology will be utilized to identify similar components. It should be understood that one or more features of other embodiments of the invention disclosed herein may be used with the embodiment of the invention illustrated in FIG. 9.

A tissue securing system 291 is used in a sterile, operating room environment and includes a suture retainer 292 and a suture 302. The suture retainer 292 includes a cylindrical central section 294 which is disposed between left and right side sections 296 and 298. The central section 294 is formed separately from the side sections 296 and 298. The side sections 296 and 298 are formed separately from each other. However, the side sections 296 and 298 could be interconnected if desired. For example, the side sections 296 and 298 could be integrally formed as one piece with a flexible connector section which extends between the side sections. Alternatively, the central section 294 and side sections 296 and 298 could be formed as one piece.

A suture 302 is wrapped around the central section 294. The suture 302 is received in a groove 304 in the central section 294. The groove 304 has a circular configuration and has a central axis which is coincident with a central axis of the cylindrical central section 294.

The groove 304 has an extent which is greater than 360° and extends completely around the central section 294 of the suture retainer 292. The groove 304 is formed as a portion of a helix. Opposite end portions of the groove 304 are disposed in an overlapping relationship on the central portion 294 of the suture retainer 292. The suture 302 is disposed in the groove 304 throughout the extent of its engagement with the central section 294.

Although the groove 304 has been shown as having somewhat more than a single turn in FIG. 8, the groove could have a plurality of turns around the central section 294 of the suture retainer 292 if desired. If this was done, the suture 302 would be wrapped a plurality of times around the central section 294. Thus, rather than having a single wrap of the suture 302 around the central section 294 of the suture retainer 292 in the manner illustrated in FIG. 9, the suture 302 could be wrapped a plurality of times around the central section of the suture retainer 294.

The suture 302 and suture retainer 292 may be formed of the same material or different materials. Similarly, the central section 294 and side sections 296 and 298 may be formed of the same material or different materials. It is believed that it may be preferred to form the suture 302 and the suture retainer 294 from biodegradable materials. However, the suture 302 and/or the suture retainer 292 could be formed of materials which are not biodegradable. It may also be preferred to form the suture retainer 292 and suture 302 of an amorphous polymeric material. The suture retainer 292 and suture 302 may be formed of any of the materials previously mentioned herein or other materials.

When the suture retainer 292 is to be utilized to secure human body tissue, the suture 302 is positioned relative to the body tissue in the manner illustrated in FIG. 4. Of course, the suture 302 could be positioned relative to body tissue in a different manner if desired. The suture 302 and suture retainer 292 may be used with hard, soft, or hard and soft body tissue.

The suture 302 is wrapped around the central section 294 of the suture retainer, in the manner illustrated schematically in FIG. 9. Once the suture 302 has been wrapped around the central section 294 of the suture retainer 292, the central section of the suture retainer is moved along the suture 302 toward the body tissue.

As the central section 294 of the suture retainer 292 moves toward the body tissue, a wrap or turn of the suture 302 around the central section of the suture retainer moves along the suture toward the body tissue. The central section 294 of the suture retainer 292 may be moved along a straight path toward the body tissue without rotating while tension is maintained in the suture 302 and the suture slides along the groove 304 in the central section of the suture retainer. Alternatively, the central section 294 of the suture retainer could be rolled along the suture 302 toward the body tissue.

The central section 294 of the suture retainer 292 is moved along the suture 302 until the central section of the suture retainer engages the body tissue in the manner illustrated in FIG. 4 or engages a force distribution member in the manner illustrated in FIG. 5. A predetermined tension force is then applied to the suture 302 and the central section 294 of the suture retainer is urged toward the body tissue with a predetermined force. The body tissue engaged by the suture 302 is compressed between the central section 294 of the suture retainer 292 and a suture anchor, similar to the suture anchor 120 of FIG. 4.

While the suture 302 is tensioned with a predetermined force and a predetermined force is transmitted from the central section 294 of the suture retainer 292 to the body tissue, the side sections 296 and 298 are aligned with the central section 294 of the suture retainer. The side sections 296 and 298 have concave surfaces 310 and 312 which are pressed against the turn in the suture 302 which extends around the central portion 294 of the suture retainer 292. The surfaces 310 and 312 have an arc of curvature which is the same as the arc of curvature of a generally cylindrical outer side surface 314 on the side sections 296 and 298. However, since the suture 302 projects out of the groove 304, the side surfaces 310 and 312 on the side sections 296 and 298 are slightly spaced from the side surface 314 on the central section 294 of the suture retainer 292.

In accordance with a feature of the present invention, ultrasonic vibratory energy is applied to the suture retainer 292. To apply the ultrasonic vibratory energy to the suture retainer 292, a support member or anvil 320 is pressed against the side section 296 of the suture retainer 292. A horn or acoustic tool 322 is pressed against the side section 298 of the suture retainer 292. The anvil 320 and horn 322 are pressed against the opposite side sections 296 and 298 of the suture retainer 292 with a predetermined force.

While the suture retainer 292 is clamped between the anvil 320 and horn 322, mechanical vibrations at an ultrasonic frequency are transmitted from the horn 322 to the suture retainer 292. The ultrasonic vibratory energy is transmitted from the horn 322 to the suture retainer 292 at frequency above 20 kilohertz. The horn 322 may transmit the ultrasonic vibratory energy to the suture retainer 292 at a frequency between 20 kilohertz and 70 kilohertz. It is contemplated that it may be desired to have the ultrasonic vibratory energy transmitted to the suture retainer at a frequency close to or greater than 70 kilohertz. However, it should be understood that the ultrasonic vibratory energy could be transmitted to the suture retainer 292 at any desired frequency above the frequency normally detected by the human ear, that is above approximately 20 kilohertz.

The ultrasonic vibratory energy transmitted to the suture retainer 292 is converted into heat. The heat tends to concentrate at the joints between the side sections 296 and 298 and central section 294 of the suture retainer 292. This results in the material forming the side sections 296 and 298 and the central section 294 of the suture retainer 292 being heated into the transition temperature range of the material forming the suture retainer. The application of the ultrasonic vibratory energy to the suture retainer 292 by the horn 322 is then interrupted.

As the material of the suture retainer 292 is heated into its transition temperature range, the material loses its rigidity and softens. The anvil 320 and horn 322 apply force against the suture retainer 292 to plastically deform the material of the suture retainer. The softened side surfaces 310 and 312 on the side sections 296 and 298 are pressed against and are indented by the suture 302. As this occurs, the softened side surfaces 310 and 312 of the side sections 296 and 298 move into engagement with the softened side surface 314 on the central section 294 of the suture retainer 292.

Although the application of ultrasonic vibratory energy to the suture retainer 292 is interrupted, the anvil 320 and horn 322 continue to be pressed against the side sections 296 and 298 of the suture retainer 292 with a predetermined force. If desired, the force with which the anvil 320 and horn 322 are pressed against the suture retainer 292 can be increased as the transmission of ultrasonic vibratory energy to the suture retainer is interrupted.

As the material of the suture retainer 292 cools, the side sections 296 and 298 are bonded to the central section 294 of the suture retainer 292. In addition, the suture 302 is bonded to the central section 294 and to the side sections 296 and 298 of the suture retainer 292.

The groove 304 in the central section 294 of the suture retainer 292 is deep enough to prevent significant deformation and loss of strength of the suture 302. As the heat softened material of the side sections 296 and 298 of the suture retainer is pressed against the suture 302, the material of the side sections is plastically deformed.

It is contemplated that bonding of the suture 302 with the central section 294 and side sections 296 and 298 of the suture retainer 292 may be promoted by forming the suture and the sections of the suture retainer of the same material. The material may be an amorphous thermoplastic which is biodegradable.

If desired, the groove 304 could be omitted from the central section 294 of the suture retainer 292. Alternatively, the groove 304 could be deepened so that the groove has a depth which is equal to or slightly greater than the diameter of the suture 302. If desired, the groove 304 could be formed with an undercut configuration so that the portion of the suture 302 in the groove 304 is not exposed to the side sections 296 and 298 of the suture retainer 292. If this was done, the suture 302 would be bonded to only the central section 294 of the suture retainer 292 and would not be bonded to the side sections 296 and 298 of the suture retainer.

If the configuration of groove 304 is changed to an undercut configuration, the suture 302 would be completely enclosed by the groove. A groove having this configuration is disclosed in U.S. Pat. No. 6,010,525 which has been and hereby is incorporated herein in its entirety. If the groove 304 has such an undercut configuration, the side sections 296 and 298 could be eliminated. The anvil 320 and horn 322 would then be pressed against opposite sides of the cylindrical outer side surface 314 of the central section 294 in the same manner as is disclosed in FIG. 8 in association with the suture retainer 270. As is disclosed in the aforementioned U.S. Pat. No. 6,010,525, the groove and suture could extend for a plurality of turns around the central portion 294 of the suture retainer 292.

In the foregoing description, it has been assumed that only ultrasonic vibrational energy may be transmitted to the suture retainer 292 to effect a bonding of the suture retainer and the suture 302. However, thermal energy in the form of heat could be directly applied to the suture retainer 292 if desired. This could be accomplished in many different ways. For example, a heating element could be provided in the anvil 320 and/or the horn 322.

Figure 10:
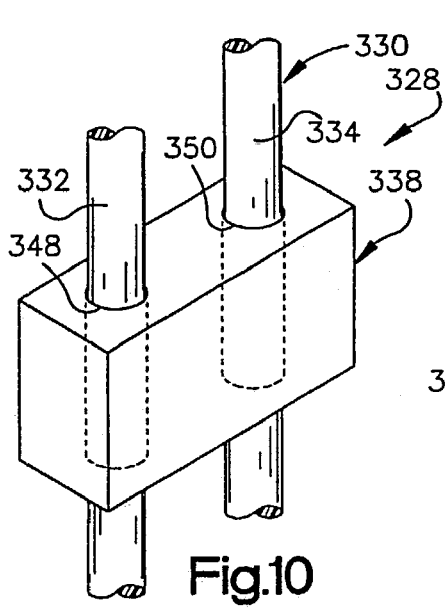
FIG. 10 is a schematic pictorial illustration of another embodiment of the invention and depicting the manner in which sections of a suture extend through passages in a section of a suture retainer.
Figure 11:
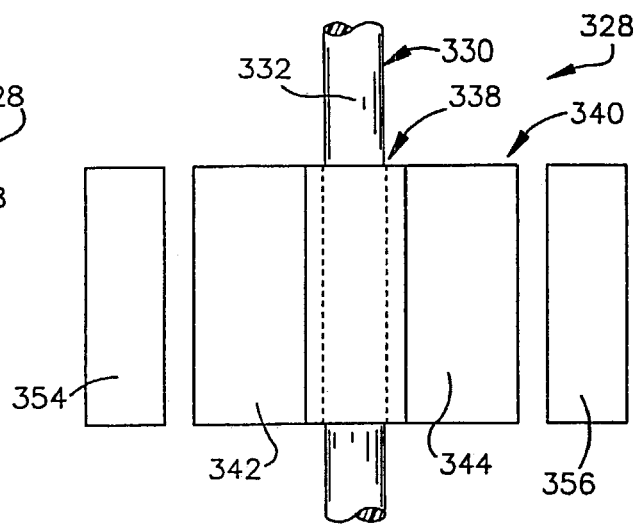
FIG. 11 is a schematic fragmentary sectional view depicting the relationship of the section of the suture retainer illustrated in FIG. 10 to other sections of the suture retainer and to an apparatus for applying ultrasonic vibratory energy to the suture retainer.

Embodiment of FIGS. 10 and 11

In the embodiment of the invention illustrated in FIG. 9, the suture 302 is wrapped around a central section 294 of the suture retainer 292. In the embodiment of the invention illustrated in FIGS. 10 and 11, sections of the suture extend through passages in a central section of the suture retainer. Since the embodiment of the invention illustrated in FIGS. 10 and 11 is generally similar to the embodiments of the invention illustrated in FIGS. 1-9, similar terminology will be utilized to identify similar components. It should be understood that one or more of the features of the other embodiments of the invention disclosed herein could be used with the embodiment of the invention illustrated in FIGS. 10 and 11 if desired.

A tissue securing system 328 is used in a sterile, operating room environment and includes a suture 330 and suture retainer 340. The suture 330 (FIGS. 10 and 11) has a pair of sections 332 and 334 which are connected with human body tissue. The sections 332 and 334 of the suture 330 may connected with body tissue in the manner illustrated schematically in FIG. 1. The sections 332 and 334 of the suture 330 extend through a central section 338 of the suture retainer 340 (FIG. 11). In addition to the central section 338, the suture retainer 340 includes a pair of side sections 342 and 344.

The central section 338 and side sections 342 and 344 all have rectangular configurations. However, the central and side sections 338, 342 and 344 (FIG. 11) could have a different configuration if desired. The central section 338 is thinner (as viewed in FIG. 11) than the side sections 342 and 344. The sections 332 and 334 of the suture 330 extend through cylindrical passages 348 and 350 in the central section 338.

The relatively thin central section 338 and the relatively thick side sections 342 and 344 of the suture retainer 340 are formed of a biodegradable material. The suture 330 is also formed of a biodegradable material. The suture 330 and suture retainer 340 may be formed of the same biodegradable material. It may be preferred to form the suture 330 and suture retainer 340 of an amorphous polymer. If desired, the suture 330 and suture retainer 340 could be formed of different materials which are compatible and have the same or similar chemical properties. The suture 330 and suture retainer 340 may be formed of any of the materials previously mentioned herein or of other known materials.

When the suture 330 and suture retainer 340 are to be used to secure human body tissue, the sections 332 and 334 of the suture 330 are positioned relative to body tissue in a manner similar to that disclosed in FIG. 1. The sections 332 and 334 of the suture 330 are then inserted through the passages 348 and 350 in the central section 338 of the suture retainer 340. While the suture 330 is tensioned, the central section 338 of the suture retainer 340 is moved along the suture toward the body tissue.

The central section 338 of the suture retainer 340 is pressed against either the body tissue in the manner illustrated schematically in FIG. 4 or against a force distribution member in the manner illustrated schematically in FIG. 5. While a predetermined force is transmitted from the central section 338 of the suture retainer 340 to the body tissue and while the sections 332 and 334 of the suture 330 are tensioned with a predetermined force, the thick side sections 342 and 344 of the suture retainer 340 are positioned in engagement with opposite sides of the thin central section 338, in the manner illustrated in FIG. 11.

An apparatus for transmitting ultrasonic vibratory energy to the suture retainer 340 is then moved into engagement with the side sections 342 and 344 of the suture retainer. The apparatus for applying ultrasonic vibratory energy to the suture retainer 340 includes an anvil or support portion 354 and a horn or acoustic tool 356. The anvil 354 and horn 356 are pressed against opposite sides of the suture retainer with a predetermined force. While the suture retainer 340 is clamped between the anvil 354 and horn 356, ultrasonic vibratory energy is transmitted from the horn 356 to the suture retainer 340.

The ultrasonic vibratory energy transmitted from the horn 356 to the suture retainer 340 is effective to heat the material of the suture retainer. The heat tends to be concentrated at the joints between the thick side sections 342 and 344 and the thin central section 338 of the suture retainer 340. In addition, the heat tends to be concentrated at the joint between the sections 332 and 334 of the suture and the central section 338 of the suture retainer. This results in a substantial portion of the material of the thin central section 338 of the suture retainer 340 being heated into its transition temperature range.

As the material of the suture retainer 340 is heated into its transition temperature range, the material of the suture retainer loses its rigidity and becomes soft. However, the material of the suture retainer is not heated enough to melt the material of the suture retainer. Since the central section 338 is relatively thin, the material of the central section becomes very pliable while the side sections 342 and 344 still have some rigidity.

Once a substantial portion of the material of the central section 338 of the suture retainer 340 has been softened by being heated into its transition temperature range, the transmission of ultrasonic vibratory energy from the horn 356 to the suture retainer 340 is interrupted. However, the anvil 354 and horn 356 continue to apply force against opposite sides of the suture retainer 340. The magnitude of the force applied against opposite sides of the suture retainer 340 by the anvil 354 and horn 356 may be increased as the transmission of ultrasonic vibratory energy from the horn 356 to the suture retainer 340 is interrupted. The force applied against opposite sides of the suture retainer 340 by the anvil 354 and horn 356 is effective to plastically deform the heat softened material of the suture retainer 340.

As the suture retainer 340 cools, the side sections 342 and 344 of the suture retainer are bonded to the central section 338 of the suture retainer. In addition, the central section 338 of the suture retainer 340 is bonded to the sections 332 and 334 of the suture 330. This results in the suture 330 being securely gripped by the suture retainer 340. However, there is no significant deformation of the suture 330 so that the strength of the suture 330 is not significantly reduced.

In the foregoing description, the material of the central section 338 of the suture retainer 340 was heated by the transmission of ultrasonic vibratory energy to the suture retainer 340. However, it is contemplated that thermal energy could be applied to the suture retainer 340 along with the ultrasonic vibratory energy. This could be accomplished by providing a heating element in the anvil 354 and/or horn 356. Alternatively, a separate member could be utilized to apply heat directly to the suture retainer 340.

The anvil 354 and horn 356 engage only the suture retainer 340. The anvil 354 and horn 356 are maintained in a spaced apart relationship with the suture 330. This prevents excessive heating and/or deformation of the suture.

Figure 12:
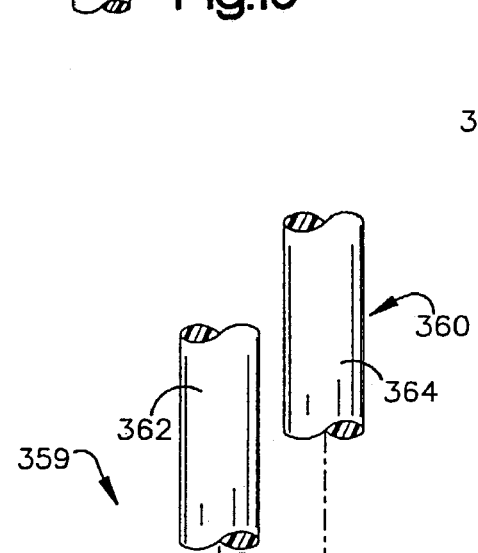
FIG. 12 is a schematic illustration of another embodiment of the invention and depicting the relationship between sections of a suture and sections of a suture retainer.
Figure 13:
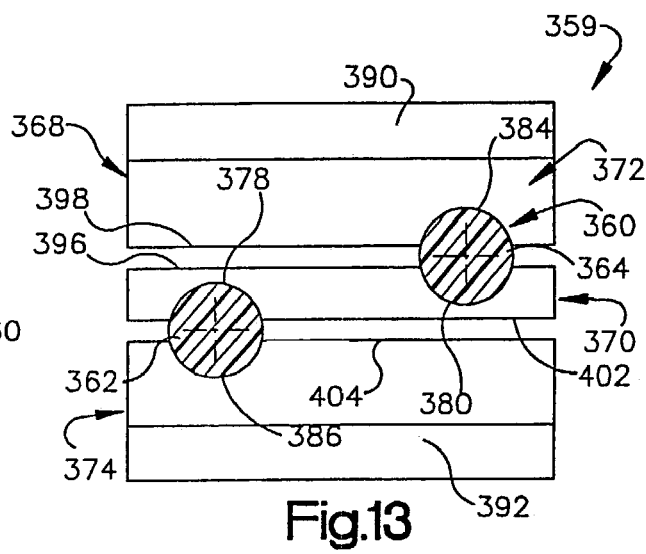
FIG. 13 is a top plan view, taken generally along the line 13-13 of FIG. 12, illustrating the relationship of the sections of the suture retainer and suture to an apparatus for applying ultrasonic vibratory energy to the suture retainer.

Embodiment of FIGS. 12 and 13

In the embodiment of the invention illustrated in FIGS. 10 and 11, the sections of the suture extend through passages in a central section of the suture retainer. In the embodiment of the invention illustrated in FIGS. 12 and 13, the sections of the suture are disposed in grooves formed in the central section of the suture retainer. Since the embodiment of the invention illustrated in FIGS. 12 and 13 is generally similar to the embodiments of the invention illustrated in FIGS. 1-11, similar terminology will be utilized to designate similar components. It should be understood that one or more of the features of other embodiments of the invention disclosed herein could be used with the embodiment of the invention illustrated in FIGS. 12 and 13.

A tissue securing system 359 (FIGS. 12 and 13) is used in a sterile, operating room environment and includes a suture 360 and a suture retainer 368. The suture 360 has left and right sections 362 and 364. The sections 362 and 364 of the suture 360 are connected with human body tissue in a manner similar to the manner illustrated schematically in FIG. 1. However, the sections 362 and 364 of the suture 360 could be connected with body tissue in a different manner if desired. For example, the sections 362 and 364 could be connected with a suture anchor embedded in the body tissue. Alternatively, a separate suture anchor could be provided for each of the sections 362 and 364 of the suture 360.

A suture retainer 368 includes a central section 370. A pair of side sections 372 and 374 are disposed on opposite sides of the central section 370. The central section 370 and side sections 374 all have a generally rectangular configuration. However, the central section 370 is thinner than the side sections 372 and 374 (FIG. 13).

A pair of grooves 378 and 380 are provided in the central section 370. The grooves 378 and 380 have parallel longitudinal central axes. The grooves 378 and 380 are disposed in opposite sides of the central section 370 and open in opposite directions.

In addition, a groove 384 is formed in the side section 372. The groove 384 extends parallel to and is aligned with the groove 380 in the central section 370. Similarly, a groove 386 is formed in the side section 374. The groove 386 extends parallel to and is aligned with the groove 378 in the central section 370. The section 362 of the suture 360 is received in the grooves 378 and 386 (FIG. 13). Similarly, the section 364 of the suture 360 is received in the grooves 380 and 384.

The grooves 378 and 386 are aligned with each other and are offset to one side of the grooves 380 and 384. This results in the sections 362 and 364 of the suture 360 being offset from each other (FIG. 13). However, if desired, the grooves 378 and 386 and the grooves 380 and 384 could all be aligned. This would result in the sections 362 and 364 of the suture being aligned with each other.

The central section 370 and side sections 372 and 374 of the suture retainer 368 are formed of a biodegradable material. The suture 360 is also formed of a biodegradable material. The suture 360 and suture retainer 368 may be formed of the same biodegradable material. It may be preferred to form the suture 360 and suture retainer 368 of an amorphous polymer. If desired, the suture 360 and suture retainer 368 could be formed of different materials which are compatible and have the same or similar chemical properties. It is contemplated that the suture 360 and suture retainer 368 could be formed of any of the materials previously mentioned herein or of other materials.

The suture 360 is positioned relative to body tissue in the same manner as is illustrated schematically in FIG. 1. While the sections 362 and 364 of the suture are tensioned with a predetermined force, the central section 370 of the suture retainer 368 is positioned relative to the sections 362 and 364 of the suture 360. In addition, the side sections 372 and 374 are positioned relative to the sections 362 and 364 of the suture and relative to the central section 370. The central section 370 and side sections 372 and 374 of the suture retainer 368 are urged toward the body tissue in the manner illustrated schematically in FIG. 4. This results in the transmission of a predetermined force from the suture retainer 360 to the body tissue while the sections 362 and 364 of the suture 360 are tensioned with a predetermined force.

In accordance with one of the features of the present invention, ultrasonic vibratory energy is then transmitted to the suture retainer 368. To transmit ultrasonic vibratory energy to the suture retainer 368, an anvil or support member 390 (FIG. 13) is pressed against the side section 372 of the suture retainer 368. In addition, a horn or acoustic tool 392 is pressed against the side section 374 of the suture retainer 368. While the suture retainer 368 is clamped between the anvil 390 and horn 392, ultrasonic vibratory energy is transmitted from the horn to the suture retainer.

The ultrasonic vibratory energy transmitted from the horn 392 to the suture retainer 368 may have a frequency in a range between 20 kilohertz and 70 kilohertz. It is believed that it will be preferred to transmit ultrasonic vibratory energy having a frequency of approximately 70 kilohertz or more from the horn 392 to the suture retainer 368.

The ultrasonic vibratory energy is effective to heat the suture retainer 368. The heat is concentrated at the joints between the thin central section 370 and thick side sections 372 and 374 of the suture retainer 368. Since the central section 370 is thinner than the side sections 372 and 374, a substantial percentage of the material of the central section 370 is heated into its transition temperature range while a smaller percentage of the material of the side sections 372 and 374 is heated into its transition temperature range.

Heating the material of the suture retainer 368 into the transition temperature range is effective to cause the material of the suture retainer to soften and lose its rigidity. Although the material of the suture retainer 368 softens, the material does not melt and become liquid. The softened material of the suture retainer is pliable and plastically deforms under the influence of the clamping force applied by the anvil 390 and horn 392.

As the material of the suture retainer 368 plastically deforms, a flat major side surface 396 on the central section 370 of the suture retainer 368 and a flat side surface 398 on the side section 372 of the suture retainer move into engagement. At the same time, a flat side surface 402 on the central section 370 of the suture retainer 368 and a flat side surface 404 on the side section 374 of the suture retainer move into engagement. As this occurs, the softened material of the central section 370 of the suture retainer 368 is deformed by force applied to the central section through the sections 362 and 364 of the suture 360.

After material of the suture retainer 368 has been heated into its transition temperature range, the application of ultrasonic vibratory energy to the suture retainer is interrupted. However, the force pressing the anvil 390 and the horn 392 against the suture retainer is maintained. If desired, the magnitude of the force applied against the suture retainer 368 by the anvil 390 and horn 392 may be increased simultaneously with the interruption of the application of ultrasonic vibratory energy to the suture retainer.

As the material of the suture retainer 368 cools, the flat major side surface 396 on the central section 370 bonds to the flat major side surface 398 on the side section 372. In addition, the flat major side surface 402 on the central section 370 bonds to the flat major side surface 404 on the side section 374. The surfaces defining the grooves 378 and 380 in the central section 370 of the suture retainer 368 bond to the sections 362 and 364 of the suture 360. The surfaces defining the grooves 384 and 386 in the side sections 372 and 374 of the suture retainer 368 also bond to the sections 362 and 364 of the suture 360.

In the foregoing description, the suture retainer 368 was heated by the application of ultrasonic vibratory energy to the suture retainer. It is contemplated that the suture retainer 368 could also be heated by the direct application of thermal energy to the suture retainer. If this is to be done, a heating element could be provided in the anvil 390 and/or horn 392. If desired, a separate heating element could be moved into engagement with the suture retainer to transmit heat to the suture retainer.

The anvil 390 and horn 392 engage only the suture retainer 368. The anvil 390 and horn 392 are maintained in a spaced apart relationship with the suture 360. This prevents excessive heating and/or deformation of the suture 360.

Embodiment of FIGS. 14 and 15

In the embodiment of the invention illustrated in FIGS. 12 and 13, straight sections 362 and 364 of the suture 360 are connected with the suture retainer 368. In the embodiment of the invention illustrated in FIGS. 14 and 15, sections of the suture are wrapped around a portion of the suture retainer. Since the embodiment of the invention illustrated in FIGS. 14 and 15 is generally similar to the embodiments of the invention illustrated in FIGS. 1-13, similar terminology will be utilized to describe similar components. It should be understood that one or more of the features of other embodiments of the invention could be utilized in association with the embodiment of the invention illustrated in FIGS. 14 and 15 if desired.

A tissue securing system 408 (FIG. 15) is used in a sterile, operating room environment and includes a suture 410 and a suture retainer 418. The suture 410 includes left and right sections 412 and 414. The left and right sections 412 and 414 of the suture 410 are connected with human body tissue in the manner illustrated schematically in FIG. 1. Alternatively, the left and right sections 412 and 414 of the suture 410 could be connected with a single suture anchor. If desired, a suture anchor could be provided in association with each of the sections 412 and 414 of the suture 410.

The suture retainer 418 (FIG. 15) includes a central section 420 and a pair of side sections 422 and 424. The central section 420 and side sections 422 and 424 of the suture retainer 418 are formed of a biodegradable material. The suture 410 is also formed of a biodegradable material. The suture 410 and suture retainer 418 may be formed of the same biodegradable material. It may be preferred to form the suture 410 and suture retainer 418 of an amorphous polymer. If desired, the suture 410 and suture retainer 418 could be formed of different materials having the same or substantially similar chemical properties. The suture 410 and suture retainer 418 could be formed of any of the materials previously mentioned herein or other materials.

When the suture retainer 418 is to be utilized to secure body tissue, the suture sections 412 and 414 are wrapped around the central section 420 of the suture retainer in the manner illustrated schematically in FIG. 14. While the sections 412 and 414 of the suture 410 are tensioned, the central section 420 of the suture retainer is moved along the suture 410 toward the body tissue. Of course, the turns or wraps formed around the central section 420 of the suture retainer 418 are moved toward the body tissue along with the central section.

The central section 420 of the suture retainer is moved into engagement with the body tissue or with a force distribution member in the manner similar to that illustrated in either FIG. 4 or FIG. 5. While a predetermined force is transmitted from the central section 420 of the suture retainer to the body tissue, the sections 412 and 414 of the suture 410 are tensioned with a predetermined force. This results in the body tissue being compressed under the influence of force being transmitted to the body tissue from the central section 420 of the suture retainer 418 and from the suture 410.

While the suture is being tensioned with a predetermined force and while the predetermined force is being transmitted from the central section 420 of the suture retainer 418, the side sections 422 and 424 are moved into juxtaposition with the central section 420 of the suture retainer 418. The side sections 422 and 424 are thicker than the central section 420. Force is also transmitted from the side sections 422 and 424 to the body tissue.

To effect the application of ultrasonic vibratory energy to the suture retainer 418, and anvil or support portion 428 is pressed against the relatively thick side section 422 of the suture retainer 418. At the same time, a horn or acoustic tool 430 is pressed against the relatively thick side section 424 of the suture retainer 418. This results in the suture retainer 418 being clamped between the anvil 428 and horn 430 with a predetermined force. The clamping force presses the suture 410 against the relatively thin central section 420 of the suture retainer.

While maintaining the predetermined clamping force on the suture retainer 418, ultrasonic vibratory energy is transmitted from the horn 430 to the suture retainer. The ultrasonic vibratory energy is transmitted at a frequency of between 20 kilohertz and 70 kilohertz. It is believed that it may be preferred to transmit the ultrasonic vibratory energy at a frequency close to or greater than 70 kilohertz.

The ultrasonic vibratory energy is effective to heat the suture retainer 418. The heat tends to be concentrated at the joints between the thin central section 420 and thick side sections 422 and 424 of the suture retainer 418. Since the central section 420 of the suture retainer 418 is thinner than the side sections 422 and 424 of the suture retainer, a larger percentage of the material of the central section 420 of the suture retainer 418 is heated into its transition temperature range by the ultrasonic vibratory energy before a corresponding percentage of the side sections 422 and 424 is heated into the transition temperature range.

When the material of the suture retainer 418 has been heated into its transition temperature range, the material becomes soft and pliable. The clamping force applied against the side sections 422 and 424 causes the turns in the sections 412 and 414 of the suture 410 to indent and plastically deform the heat softened material of the central section 420 and side sections 422 and 424. As this occurs, the side sections 422 and 424 move into abutting engagement with the central section 410 under the influence of the clamping force applied by the anvil 428 and horn 430.

Once the material of the central section 420 and side sections 422 and 424 adjacent to the turns in the sections 412 and 414 of the suture 410 have been heated into the transition temperature range, the application of ultrasonic vibratory energy to the suture retainer 418 is interrupted. However, the clamping force applied against the suture retainer by the anvil 428 and horn 430 is maintained constant or increased as the application of ultrasonic vibratory energy to the suture retainer is interrupted. As the material of the suture retainer 418 cools, while the suture retainer is clamped between the anvil 428 and horn 430, the side sections 422 and 424 of the suture retainer 418 bond to the central section 420 of the suture retainer. In addition, the side sections 422 and 424 and the central section 420 of the suture retainer 418 bond to the suture 410.

Embodiment of FIGS. 16 and 17

In the embodiments of the invention illustrated in FIGS. 9 through 15, the suture retainer is formed by a plurality of sections which are bonded together. In the embodiment of the invention illustrated in FIGS. 16 and 17, the suture retainer is formed as one piece. Since the suture retainer in the embodiment of FIGS. 16 and 17 is generally similar to the suture retainers of FIGS. 1-16, similar terminology will be utilized to identify similar components. It should be understood that one or more of the features of any of the other embodiments of the invention disclosed herein could be utilized with the embodiment of the invention illustrated in FIGS. 16 and 17.

A tissue securing system 438 is used in a sterile, operating room environment and includes a suture 440 and a suture retainer 448. The suture 440 includes left and right sections 442 and 444. The left and right sections 442 and 444 of the suture 440 are connected with human body tissue in a manner similar to the manner illustrated schematically in FIG. 1. However, the suture 440 could be connected with body tissue in a different manner if desired. For example, the sections 442 and 444 could be connected with a single suture anchor embedded in body tissue. Alternatively, a separate suture anchor could be provided for each of the sections 442 and 444 if desired.

A one-piece suture retainer 448 is formed separately from the suture 440. The suture retainer 448 has a generally H-shaped configuration. The suture retainer 448 includes a rectangular base section 450 and a pair of arm sections 452 and 454. The arm sections 452 and 454 are connected with the base section 450 by a connector section 456. Although only the one side, which may be considered as the top side of the suture retainer 448 is illustrated in FIG. 16, the suture retainer has a generally rectangular configuration. The extent of the suture retainer 448 along the sections 442 and 444 of the suture 440 may be equal to the distance between longitudinal central axes of the sections of the suture.

The suture retainer 448 has a pair of recesses 460 and 462 in which the sections 442 and 444 of the suture 440 are received. An entrance 466 to the recess 460 (FIG. 17) is partially blocked by a nose or detent portion 468 of the arm section 452. When the suture section 442 is to be moved into the recess 460, the cylindrical outer side surface of the suture section 442 is pressed against a cam surface 472 on the nose portion 468 of the arm section 452. Force applied against the cam surface 472 resiliently deflects the arm section 452 away from the base section 450 from the position shown in solid lines in FIG. 17 to the position shown in dashed lines. As this occurs, the section 442 of the suture 440 moves into the recess 460. As the section 442 of the suture 440 moves into the recess 460, the arm section 452 springs back to the initial position shown in solid lines in FIG. 17 to block the entrance 446 to the recess 460. This results in the suture section 442 being retained in the recess 460.

The arm section 454 has the same construction as the arm section 452. Thus, the arm section 454 has a nose or detent portion 476 (FIG. 16) which is engaged by the suture section 444 to deflect the arm section 454 as the suture section moves into the recess 462. Once the suture section 444 has moved into the recess 462, the nose portion 476 on the arm section 454 blocks the entrance to the recess to retain the suture section 444 in the recess.

The suture 440 and suture retainer 448 are both formed of a biodegradable polymer. It is believed that it may be preferred to form the suture retainer 448 and suture 440 from an amorphous thermoplastic. The suture 440 and suture retainer 448 may be formed of the same material or different materials having similar chemical properties which are compatible. The suture 440 and suture retainer 448 may be formed of any of the materials previously mentioned herein or of other materials.

When the suture 440 and suture retainer 448 are to be utilized to secure human body tissue, the suture 440 is positioned relative to the body tissue, in a manner similar to that illustrated schematically in FIG. 1. The sections 442 and 444 of the suture 440 are then moved into the recesses 460 and 462 in the suture retainer 448. The nose portions 468 and 476 on the arm sections 452 and 454 are effective to retain the suture sections 442 and 444 in the recesses 460 and 462.

While the suture sections 442 and 444 are tensioned, the suture retainer 448 is moved along the suture 440 toward the body tissue. The nose portions 468 and 476 on the arm sections 452 and 454 maintain the suture sections 442 and 444 in the recesses 460 and 462 as the suture retainer 448 is moved along the suture 440 toward the body tissue. The suture retainer 448 is moved into engagement with either the body tissue, in the manner similar to that illustrated in FIG. 4, or into engagement with a force distribution member, in the manner similar to that illustrated in FIG. 5.

While a predetermined tension force is applied to the sections 442 and 444 of the suture 440 and while the suture retainer 448 is urged toward the body tissue with a predetermined force, the suture retainer 448 is bonded to the suture 440. This results in a predetermined tension being maintained in the portion of the suture 440 connected with the body tissue and in the transmission of a predetermined force from the suture retainer 448 to the body tissue.

To bond the suture 440 to the suture retainer 448, an anvil or support portion 480 is pressed against the base section 450 of the suture retainer 448. A horn or acoustic tool 482 is pressed against the arm sections 452 and 454 of the suture retainer 448. The arm sections 452 and 454 of the suture retainer 448 have protuberances 486 and 488 which extend toward the horn 482.

The suture retainer 448 is clamped between the anvil 480 and horn 482. The force applied against the arm sections 452 and 454 by the horn 482 resiliently deflects the arm sections toward the base section 450 of the suture retainer 448. This results in the nose portions 468 and 476 on the arm sections 452 and 454 moving into engagement with the base section 450. Protuberances 486 and 488 on the arm sections 452 and 454 enable the horn 482 to deflect the arm sections through a sufficient distance to enable the arm sections to engage the base section 450.

Once the suture retainer 448 has been securely clamped between the anvil 480 and horn 482, ultrasonic vibratory energy is transmitted from the horn 482 to the suture retainer 448. The ultrasonic vibratory energy transmitted from the horn 482 to the suture retainer 448 is at a frequency of between 20 kilohertz and 70 kilohertz. It is believed that it may be preferred to apply ultrasonic vibratory energy at a frequency of approximately 70 kilohertz or more to the suture retainer 448.

The ultrasonic vibratory energy transmitted from the horn 482 to the suture retainer 448 is effective to heat the material of the suture retainer. The heat tends to be concentrated at the joints between the arm sections 452 and 454 and the base section 450. In addition, the heat tends to be concentrated at the joints between the suture sections 442 and 444 and the suture retainer 448.

The material of the suture retainer 448 is heated into a transition temperature range for the material. As the material of the suture retainer 448 is heated into the transition temperature range, the material of the suture retainer softens and becomes pliable. However, the material of the suture retainer 448 does not melt and become a liquid.

The heat softened material of the suture retainer 448 is plastically deformed by the force applied against the suture retainer by the anvil 480 and horn 482. As the material of the suture retainer 448 is plastically deformed, the recesses 460 and 462 are collapsed. The material of the suture retainer 448 is firmly pressed against the suture 440.

Once the material of the suture retainer 448 adjacent to the sections 442 and 444 of the suture and adjacent to the nose portions 468 and 476 on the arm sections has been heated into a transition temperature range and plastically deformed, the application of ultrasonic vibratory energy is interrupted. Heating the material of the suture retainer 448 into its transition temperature range causes the material to lose its rigidity and soften. The heat softened material of the suture retainer 448 can be deformed by the clamping force applied by the anvil 480 and horn 482.

Although the application of ultrasonic vibratory energy to the suture retainer 448 is interrupted, the suture retainer continues to be clamped between the anvil 480 and horn 482. If desired, the clamping force applied against the suture retainer 448 by the anvil 480 and horn 482 could be increased as the application of ultrasonic vibratory energy to the suture retainer is interrupted.

As the material of the suture retainer cools, the arm sections 452 and 454 of the suture retainer are bonded to the base section 450 of the suture retainer. In addition, the arm sections 452 and 454, connector section 456 and base section 450 of the suture retainer 448 are bonded to the sections 442 and 444 of the suture 440. This results in the suture 440 and the suture retainer 448 being securely interconnected.

In the foregoing description, the suture retainer 448 has been heated under the influence of ultrasonic vibratory energy transmitted from the horn 482 to the suture retainer. It is contemplated that the suture retainer 448 could also be heated by the direct application of thermal energy to the suture retainer. For example, a heating element could be provided in the anvil 480 and/or the horn 482 to function as a heat source. Alternatively, a heating element could be moved into contact with the suture retainer 448.

The anvil 480 and horn 482 do not engage the suture 440. The anvil 480 and horn 482 engage only the suture retainer 448. This prevents excessive heating and deformation of the suture 440. There is no significant deformation of the suture 440 so that it maintains its strength.

Embodiment of FIGS. 18-20

In the embodiment of the invention illustrated in FIGS. 16 and 17, the sections 442 and 444 of the suture 440 are positioned in a pair of recesses 460 and 462 in the suture retainer 448. In the embodiment of the invention illustrated in FIGS. 18-20, a single section of a suture is positioned in a single recess in a suture retainer. Since the suture retainer of the embodiment of the invention illustrated in FIGS. 18-20 is generally similar to the suture retainers of the embodiments of the invention illustrated in FIGS. 1-17, similar terminology will be utilized to identify similar components. It should be understood that one or more of the features of the other embodiments of the invention disclosed herein could be utilized in association with the embodiment of the invention illustrated in FIGS. 18-20.

A tissue securing system 489 (FIG. 18) is used in a sterile, operating room environment and includes a suture 490 and a suture retainer 496. The suture 490 (FIG. 18) has a section 492 which is connected with human body tissue in a manner generally similar to the manner illustrated schematically in FIG. 4. The suture section 492 may be connected with a suture anchor disposed in engagement with one side of a layer of body tissue. Alternatively, the suture section 492 may be connected with a suture anchor which is embedded in body tissue. The suture 490 could be connected with a suture anchor having a construction generally similar to the construction of the suture anchors disclosed in U.S. Pat. Nos. 5,584,862; 5,549,631; and/or 5,527,343.

A one-piece suture retainer 496 includes main sections 498 and 500. The main sections 498 and 500 of the suture retainer 496 are interconnected by a hinge section 502. The suture retainer 496 is formed separately from the suture 490.

The main sections 498 and 500 and hinge section 502 of the suture retainer 496 are integrally formed as one piece. The suture 490 and suture retainer 496 are both formed of a biodegradable polymer. It is believed that it may be preferred to form the suture 490 and suture retainer 496 from the same amorphous thermoplastic material. However, the suture 490 and suture retainer 496 may be formed of different amorphous thermoplastic materials having similar chemical properties. The suture 490 and suture retainer 496 may be formed from any of the materials previously mentioned herein or other materials.

The main sections 498 and 500 of the suture retainer 496 are initially skewed at an angle of approximately 30° to each other. The main sections 498 and 500 cooperate with the hinge section 502 to define a generally V-shaped recess 506 (FIG. 19) in which the section 492 of the suture is received. If desired, the recess 506 could have a configuration which is different than the illustrated V-shaped configuration.

While a predetermined tension is maintained in the suture 490, the suture retainer 496 is moved along the suture into engagement with the body tissue, in a manner generally similar to the manner illustrated in FIG. 4 or into engagement with a force distribution member, in the manner generally similar to the manner illustrated in FIG. 5. While a predetermined force is being transmitted from the suture retainer 496 to the body tissue and while the suture 490 is being tensioned with a predetermined force, the suture 490 is bonded to the suture retainer 496 and the main sections 498 and 500 of the suture retainer 496 are bonded together.

To effect bonding between the suture retainer 496 and the suture 490, an anvil 512 (FIG. 20) is moved into engagement with the main section 498 of the suture retainer 496. At the same time, a horn or acoustic tool 514 is moved into engagement with the main section 500 of the suture retainer 496. The anvil 512 and horn 514 apply force against the suture retainer 496 to clamp the suture retainer against the suture 490.

As the anvil 512 and horn 514 are clamped against the suture retainer 496, the main sections 498 and 500 of the suture retainer are deflected from the linear configuration illustrated in FIG. 19 to the bent configuration illustrated in FIG. 20. The anvil 512 and horn 514 have a configuration which corresponds to the desired configuration of the suture retainer 496 when the suture retainer is clamped against the suture 490 by the anvil and horn.

The suture retainer 496 is heated to effect a bonding between the main sections 498 and 500 of the suture retainer and to effect a bonding between the suture 490 and the main sections 498 and 500 and the hinge section 502 of the suture retainer. To effect this bonding, ultrasonic vibratory energy is transmitted from the horn 514 to the suture retainer 496. The ultrasonic vibratory energy transmitted from the horn 514 to the suture retainer 496 has a frequency of between 20 kilohertz and 70 kilohertz. It is believed that it may be preferred to transmit ultrasonic vibratory energy having a frequency of 70 kilohertz or more from the horn 514 to the suture retainer 496.

The ultrasonic vibratory energy transmitted from the horn 514 to the suture retainer 496 heats the material of the suture retainer. The heat tends to be concentrated at the joints between the main section 498 and 500 of the suture retainer and at the joints between the suture 490 and the main sections 498 and 500 and the hinge section 502 of the suture retainer. The material of the suture retainer 496 is heated into a transition temperature range for the material.

When the material adjacent to the main sections 498 and 500 of the suture retainer 496 and adjacent to the joint between the suture 490 and the suture retainer 496 has been heated into a transition temperature range, the application of ultrasonic vibratory energy to the suture retainer 496 is interrupted. Although the application of ultrasonic vibratory energy from the horn 514 to the suture retainer 496 is interrupted, the suture retainer continues to be clamped between the anvil 512 and the horn 514. If desired, the force applied against the suture retainer 496 by the anvil 512 and horn 514 could be increased simultaneously with interruption of ultrasonic vibratory energy to the suture retainer 496.

As the material of the suture retainer 496 is heated into its transition temperature range, the material softens and loses its rigidity. Although the material of the suture retainer 496 softens as the material is heated into its transition temperature range, the material does not melt and become liquid. As the material of the suture retainer 496 softens, the force applied against the suture retainer 496 by the anvil 512 and horn 514 plastically deforms the suture retainer from the configuration illustrated in FIG. 19 to the configuration illustrated in FIG. 20.

As the material of the suture retainer 496 cools, a bond is formed between the main sections 498 and 500 of the suture retainer. In addition, the main sections 498 and 500 and the hinge section 502 of the suture retainer 496 are bonded to the suture 490. This results in the suture retainer 496 having a firm grip on the suture 490. The firm grip of the suture retainer 496 on the suture 490 enables a predetermined tension force to be transmitted through the suture 490 to the body tissue and enables a predetermined force to be transmitted from the suture retainer 496 to the body tissue.

The anvil 512 and horn 514 do not engage the suture 490. The anvil 512 and horn 514 engage only the suture retainer 496. This prevents excessive heating and deformation of the suture 490. The suture retainer 496 is bonded to the suture 490 without significant deformation of the suture.

In the embodiment of the invention illustrated in FIGS. 18-20, a single section 492 of the suture 490 is engaged by the suture retainer 496. However, a plurality of sections of suture could be gripped by the suture retainer 496. Thus, a pair of suture sections, corresponding to the suture sections 182 and 184 of FIG. 5, could be positioned in the recess 506 (FIG. 19) in the suture retainer 496 and gripped by the suture retainer. If desired, a force distribution member corresponding to the force distribution member 194 of FIG. 5 could be provided between the suture retainer 496 and the body tissue.

Embodiment of FIG. 21

In the embodiment of the invention illustrated in FIGS. 18-20, the suture retainer 496 includes a pair of main sections 498 and 500 which are interconnected by a flexible hinge section 502 and which define a recess 506 in which the suture 490 is received. In the embodiment-of the invention illustrated in FIG. 21, one section of a suture retainer cooperates with another section of the suture retainer to define a recess in which a suture is received. Since the embodiment of the invention illustrated in FIG. 21 is generally similar to the embodiment of the invention illustrated in FIGS. 1-20, similar terminology will be utilized to identify similar components. It should be understood that one or more of the features of the other embodiments of the invention illustrated herein could be used with the embodiment of the invention illustrated in FIG. 21.

A tissue securing system 518 is used in a sterile, operating room environment and includes a suture 520 and a suture retainer 528. The suture 520 (FIG. 21) includes a section 522 which is connected with body tissue. The section 522 of the suture 520 may be connected with body tissue in the manner illustrated schematically in FIG. 4. However, it should be understood that the suture 520 could be connected with body tissue in a different manner if desired.

The suture retainer 528 is formed separately from the suture 520 and encloses a portion of the suture. The suture retainer 528 has a rectangular configuration and includes a base section 530 and an arm section 532. The base and arm sections 530 and 532 of the suture retainer 528 are integrally formed as one piece. The arm section 532 cooperates with the base section 530 to define a generally U-shaped recess 534 in which the suture 520 is received.

The suture retainer 528 may have a configuration which is different than the configuration illustrated in FIG. 21. For example, the suture retainer 528 could have an ovoidal configuration rather than the illustrated rectangular configuration. Although the base section 530 has been illustrated as being substantially wider than the arm section 532, the base and arm sections could be of approximately the same width if desired. The base and arm sections 530 and 532 could have configuration similar to the configuration of the base section 450 and arm section 452 of FIG. 16 if desired. If desired, the recess 534 could have a different configuration. For example, the recess 534 could have a configuration similar to the configuration of the recess 460 of FIG. 16.

The suture retainer 528 may be formed of any one of many different materials, including any of the materials previously mentioned herein. It may be preferred to form the suture retainer 528 of a biodegradable material. The suture 520 may be formed of the same biodegradable material as the suture retainer 528. It is believed that it may be preferred to form both the suture 520 and suture retainer 528 of an amorphous polymer, such as polyhydroxyalkanoate. Of course, the suture 520 and suture retainer may be formed of other materials if desired.

When the suture 520 and suture retainer 528 are to be utilized to secure body tissue, the suture 520 is positioned relative to body tissue by engagement with a suture anchor or other device. The suture 520 is then positioned in the recess 534 in the suture retainer 528. The suture 520 may be positioned in the recess 534 by moving the suture through an entrance to the recess. Alternatively, the suture retainer 528 could be moved relative to the suture.

Once the suture 520 has been positioned in the recess 534, a predetermined tension force is applied to the suture 520. The suture retainer 528 is moved along the suture toward the body tissue. The suture retainer is pressed against the body tissue in the manner illustrated schematically in FIG. 4 or pressed against a force distribution member in the manner illustrated schematically in FIG. 5. A predetermined force is transmitted from the suture retainer 528 to the body tissue while the predetermined tension is maintained in the suture 520.

To interconnect the suture 520 and suture retainer 528, the suture retainer is clamped between a horn and anvil of an ultrasonic energy application apparatus. Ultrasonic energy is then transmitted from the horn to the suture retainer 528 in the manner previously described in conjunction with the embodiments of the invention illustrated in FIGS. 1-20.

The clamping force applied against the suture retainer 528 by the horn and anvil deflects the arm section 532 of the suture retainer toward the base section 530 of the suture retainer. The arm section moves into engagement with the base section 530 of the suture retainer 528 and firmly grips the suture 520 under the influence of the clamping force applied by the anvil and horn.

Ultrasonic energy at a frequency of between 20 kilohertz and 70 kilohertz is then applied to the suture retainer 528 by the horn. The ultrasonic vibratory energy heats the material of the suture retainer 528 into its transition temperature range. As the material of the suture retainer 528 is heated into the transition temperature range, the material of the suture retainer softens and loses its rigidity. As this occurs, the softened material of the suture retainer 528 is plastically deformed by the clamping force applied against the suture retainer by the anvil and horn.

The transmission of ultrasonic vibratory energy to the suture retainer 520 is then interrupted. However, the clamping force against the suture retainer is maintained and may even be increased.

As the material of the suture retainer 528 cools, the suture retainer 528 is securely connected to the suture 520. Thus, the arm section 532 is bonded to the base section 530 of the suture retainer. Both the base section 530 and the arm section 532 are bonded to the suture 520. This results in the suture retainer 528 having a firm grip on the suture 520 to maintain the tension in the suture and the transmission of force from the suture retainer to body tissue.

Embodiment of FIG. 22

In the embodiment of the invention illustrated in FIG. 21, the arm section 532 is generally straight and cooperates with the base section 530 to form a recess 534. In the embodiment of the invention illustrated in FIG. 22, the suture retainer has an arcuate arm section which cooperates with a base section to form a recess which receives a suture. Since the embodiment of the invention illustrated in FIG. 22 is generally similar to the embodiments of the invention illustrated in FIGS. 1-21, similar terminology will be utilized to designate similar components. It should be understood that one or more of the features of the other embodiments of the invention disclosed herein could be utilized in conjunction with the embodiment of the invention illustrated in FIG. 22.

A suture 540 is connected with body tissue in the manner illustrated schematically in FIG. 4. A suture retainer 542 at least partially encloses the suture 540. The suture retainer 542 is integrally formed as one piece which is separate from the suture 540.

The suture retainer 542 includes a base section 544 and an arm section 546. The base section 544 and arm section 546 of the suture retainer are integrally formed as one piece. The suture retainer 542 has the same generally rectangular configuration as the suture retainer 528 of FIG. 21. However, the suture retainer 542 could have a different configuration if desired.

The suture retainer 542 may be formed of a biodegradable polymeric material. It is believed that it may be preferred to form both the suture 540 and the suture retainer 542 from the same biodegradable polymeric material. The suture 540 and suture anchor may be formed from an amorphous thermoset polymer. If desired, the suture retainer 542 and suture 540 could be formed of different polymeric materials which are compatible with each other. The suture 540 and suture retainer 542 could be formed from many different materials, including any of the materials mentioned herein.

The arm section 546 of the suture retainer 542 cooperates with the base section 544 of the suture retainer to define a recess 550 which receives a portion of the suture 540. The arm section 546 has a nose portion 554 which partially blocks an entrance 556 to the recess 550. The nose portion 554 on the arm section 546 is effective to retain the suture 540 in the recess 550.

When the suture 540 and suture retainer 542 are to be utilized to secure body tissue, the suture 540 is positioned relative to the body tissue in a manner similar to that illustrated in FIG. 4. Of course, the suture 540 could be connected with the body tissue in a different manner if desired. For example, the suture 540 could be connected with a suture anchor which is embedded in the body tissue.

Once the suture 540 has been positioned relative to the body tissue, the suture is tensioned and positioned in the recess 550 in the suture retainer 542. To position the suture 540 in the recess 550, the suture can be moved relative to the recess or the recess can be moved relative to the suture.

As the suture 540 moves into the recess 556, the a cylindrical outer side surface of the suture applies force against a cam surface 558 on the nose portion 554 of the arm section 546. The force applied against the cam surface 558 deflects the arm section 546 outward away from the base section 544 of the suture retainer 542 to open the entrance 556 to the recess 550. This enables the suture 540 to move into the recess 550.

After the suture 540 has moved into the recess 550, the arm section 546 springs back to its initial position, illustrated in FIG. 22. When this occurs, the nose portion 554 on the arm section 546 partially blocks the entrance 556 to the recess 550 to retain the suture 540 in the recess.

Once the suture 540 has been positioned in the recess 550, the suture 540 is tensioned with a predetermined force and the suture retainer 542 is moved along the suture toward the body tissue. The suture retainer 542 is moved into engagement with the body tissue in the manner illustrated in FIG. 4 or is moved into engagement with a force distribution member in the manner illustrated in FIG. 5. A predetermined force is transmitted from the suture retainer 542 to the body tissue while the predetermined tension is maintained in the suture 540. This results in layers of body tissue being pressed against each other.

The suture retainer 542 and suture 540 are then interconnected to maintain the predetermined tension in the portion of the suture 540 connected with the body tissue and to maintain the transmission of the predetermined force from the suture retainer to the body tissue. To interconnect the suture retainer 542 and suture 540, the suture retainer is clamped between an anvil 562 and a horn 564 of an ultrasonic energy application apparatus. The clamping force applied against the suture retainer 542 by the anvil 562 and horn 564 resiliently deflects the arm section 546 so that the nose portion 554 of the arm section moves into engagement with the base section 544 of the suture retainer. In addition, the arm section 546 is firmly pressed against the suture 540.

While the clamping force is applied to the suture retainer 542 by the anvil 562 and horn 564, ultrasonic vibratory energy is transmitted from the horn to the suture retainer. The ultrasonic vibratory energy has a frequency of between 20 kilohertz and 70 kilohertz. It is believed that it may be preferred to utilize ultrasonic vibratory energy having a frequency of approximately 70 kilohertz or more.

The ultrasonic vibratory energy heats the material of the suture retainer into its transition range. The heat tends to be concentrated at the joint between the arm section 546 and the base section 544 of the suture retainer 542. In addition, the heat is concentrated at the joint between the suture 540 and the suture retainer 542.

Once the material of suture retainer 542 has been softened by being heated into its transition temperature range, the application of ultrasonic vibratory energy to the suture retainer is interrupted. Even though the application of ultrasonic vibratory energy to the suture retainer is interrupted, the clamping force applied against the suture retainer 542 by the anvil 562 and horn 564 is maintained or even increased.

As the material of the suture retainer 542 cools, a secure bond is formed between the arm section 546 and the base section 544 of the suture retainer. In addition, a secure bond is formed between the suture 540 and the base section 544 and arm section 546 of the suture retainer 542.

Figure 23:
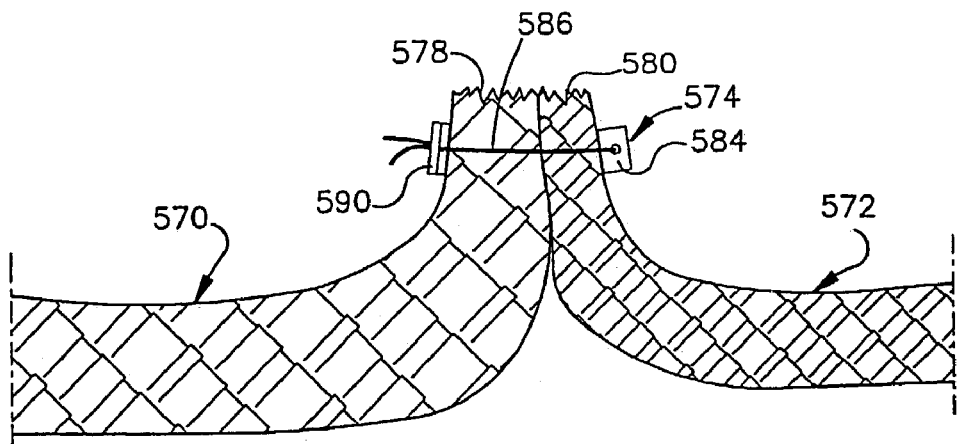
FIG. 23 is a schematic illustration of another embodiment of the invention and depicting the manner in which a suture and a suture retainer are utilized to hold layers of body tissue in apposition with each other.

Embodiment of FIG. 23

In the embodiments of the invention illustrated in FIGS. 1-22, various types of suture retainers for use in securing a suture relative to body tissue have been illustrated. The embodiment of the invention illustrated in FIG. 23 is not limited to any particular suture retainer construction. However, similar terminology will be utilized in describing the components of the embodiment of the invention illustrated in FIG. 23 as were previously utilized in connection with the embodiments of the invention illustrated in FIGS. 1-22.

In the embodiment of the invention illustrated in FIG. 23, a relatively thick layer of tissue, designated by the numeral 570, is to be connected with a relatively thin layer of tissue, designated by the numeral 572. A tissue securing system 574 is utilized to interconnect the thick and thin layers of tissue. The tissue securing system 574 is located a precise distance from an end 578 of the thick layer 570 of tissue and an end 580 of the thin layer 572 of tissue.

In the illustrated embodiment of the invention, the tissue securing system 574 is located the same distance from the end 578 of the thick layer of tissue as in which the tissue fixation system is located from the end 580 of the thin layer of tissue. This results in the two layers of tissue growing together with a minimum of scarring. In addition, the tissue securing system 574 holds the thick layer 570 and the thin layer 572 of tissue against shifting relative to each other.

If a staple of loop-type suture was used to interconnect the thick layer 570 and thin layer 572 of tissue, a shifting could occur between the two layers of tissue. This shifting could occur inside of the loop formed by the suture or the staple. The shifting can result in extensive scarring and could result in a non-uniform repair of the tissue. The obtaining of a uniform repair of tissue is particularly important when interconnecting a conduit, such as a blood vessel, which has been severed. By using the tissue securing system 574, shifting movement can not occur between the thick layer 570 and thin layer 572 of tissue. This prevents one of the layers from being deflected into the path of flow of material, such as blood, through the conduit in a manner which restricts the conduit and subsequently results in a blockage.

The specific tissue securing system 574 illustrated in FIG. 23 includes a suture anchor 584 which is disposed in engagement with an outer side surface of the thin layer 572 of tissue. A suture 586 extends through both the thin layer 572 of tissue and the thick layer 570 of tissue. The suture 586 is disposed the same distance from the end 578 of the thick layer 570 of tissue as it is located from the end 580 of the thin layer 572 of tissue. A suture retainer 590 is connected with a portion of the suture 586 opposite from the anchor 584. The suture retainer 590 may have any one of the constructions described herein or a different construction.

In accordance with a feature of the present invention, the suture retainer 590 is connected with the suture 586 by the application of ultrasonic vibratory energy to the suture retainer 590. The application of ultrasonic vibratory energy to the suture retainer 590 results in a rapid heating of the material of the suture anchor. The very short time which is required to heat the material of the suture retainer 590 by the application of ultrasonic vibratory energy enables the suture retainer to be heated into its transition temperature range and softened without detrimentally affecting the layers 570 and 572 of body tissue.

Although it is contemplated that the amount of heat which is required to heat material of the suture retainer 590 into the transition temperature range by the application of ultrasonic vibratory energy will vary depending upon the construction of the suture retainer 590, an ultrasonic vibratory energy application time of between 0.25 seconds and 1.0 seconds is required to connect any one of the suture retainers of FIGS. 1-22 with a suture. After the suture retainer 590 has been heated and the application of ultrasonic vibratory energy interrupted, the suture retainer is allowed to cool for approximately one second. Since the suture retainer 590 is heated into its transition temperature range for an extremely short period of time, the suture retainer can be heated to relatively high temperatures which would be detrimental to the layers 570 and 572 of the body tissue if the application of ultrasonic vibratory energy was maintained over an extended period of time.

In the embodiments of the invention illustrated in FIGS. 1, 4 and 23, the tissue securing systems are being utilized to interconnect layers of soft tissue disposed in juxtaposition with each other. However, it contemplated that the tissue securing system could be utilized to interconnect body tissues having different characteristics. For example, the tissue securing system could be utilized to connect soft tissue, such as a tendon, or ligament, with bone. If the tissue securing system was utilized to connect soft tissue with bone, the suture anchor would engage the bone in a manner similar to that disclosed in U.S. Pat. No. 5,403,348 and/or 5,534,012. The suture would then extend from the anchor positioned in the bone into engagement with the soft body tissue. The suture could be wrapped around the soft body tissue or, alternatively, could extend through the soft body tissue. A suture retainer having any of the constructions illustrated in FIGS. 1-22 could be connected with one or two sections of the suture to hold the soft body tissue in place relative to the bone.

Although it is preferred to connect the suture retainers illustrated in FIGS. 1-22 with a suture, the suture retainers could be connected with other force transmitting members or directly with body tissue if desired. For example, any one of the suture retainers of FIGS. 1-22 could be connected with a K-wire or a rigid force transmitting member such as a rod or externally threaded stud. Alternatively, the suture retainer could be connected directly to body tissue, such as a ligament or tendon.

In the embodiments of the invention illustrated in FIGS. 1-22, the suture retainers have been connected with sutures formed of polymeric material. However, the sutures could be formed of metal if desired. Thus, the suture retainers illustrated in FIGS. 1-22 could be connected with any desired type of member which transmits force, including body tissue.

It is contemplated that the suture retainers illustrated in FIGS. 1-22 will be utilized in an operating room environment. The suture retainers may be positioned within and fully enclosed by a patient's body. Alternatively, the suture retainers may be partially disposed outside of the patient's body.

Figure 24:
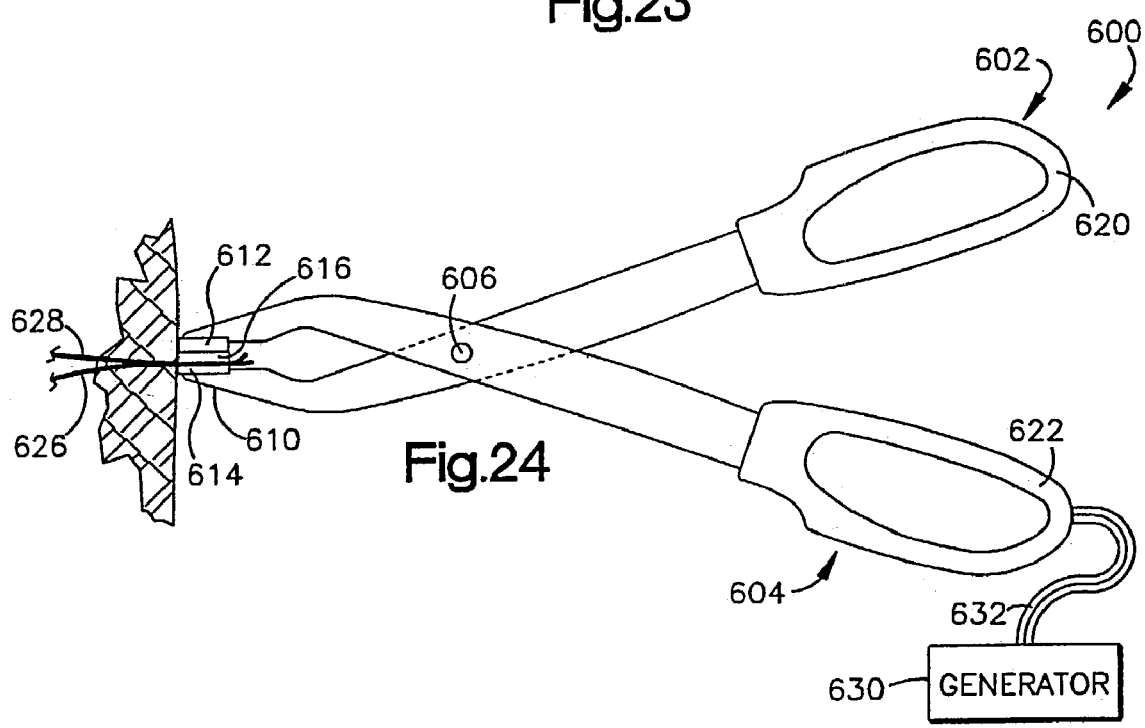
FIG. 24 is a schematic illustration of one apparatus for applying ultrasonic vibratory energy to a suture retainer.

Embodiment of FIG. 24

It is contemplated that the suture retainers of FIGS. 1-23 may be heated by the application of ultrasonic vibratory energy. The ultrasonic vibratory energy may be applied in many different ways. One known apparatus for applying the ultrasonic vibratory energy to any one of the suture retainers of FIGS. 1-23 is illustrated schematically in FIG. 24.

An ultrasonic vibratory energy application apparatus 600 includes a pair of members 602 and 604 which are interconnected at a pivot connection 606. An anvil or support member 610 is mounted on one end portion of the member 602. A horn or ultrasonic energy application member 612 is mounted on one end portion of the member 604.

Sections 614 and 616 of a suture retainer are disposed in engagement with the anvil 610 and horn 612. The sections 614 and 616 of the suture retainer may have the same construction as the sections 222 and 224 of the suture retainer 220 of FIG. 6. When handle end portions 620 and 622 of the members 602 and 604 are moved together, the anvils 610 and horn 612 press the sections 614 and 616 of the suture retainer against sections 626 and 628 of a suture.

A generator 630 is connected with a standard electrical power supply (120-240 volts). The generator 630 converts the standard electrical power supply from 50/60 hertz to an ultrasonic frequency, that is a frequency greater than 20 kilohertz. The high frequency electrical energy is conducted through a cable 632 to the member 604.

Suitable electrically insulated conductors in the member 604 conduct the high frequency electrical energy through a transducer (not shown) connected with the horn. The transducer changes the electrical energy into low amplitude mechanical vibrations. These vibrations may be transmitted to a booster to increase or decrease the amplitude of the vibrations. The vibrations are then transmitted to the horn 612 which applies them to the sections 614 and 616 of the suture retainer.

Figure 25:
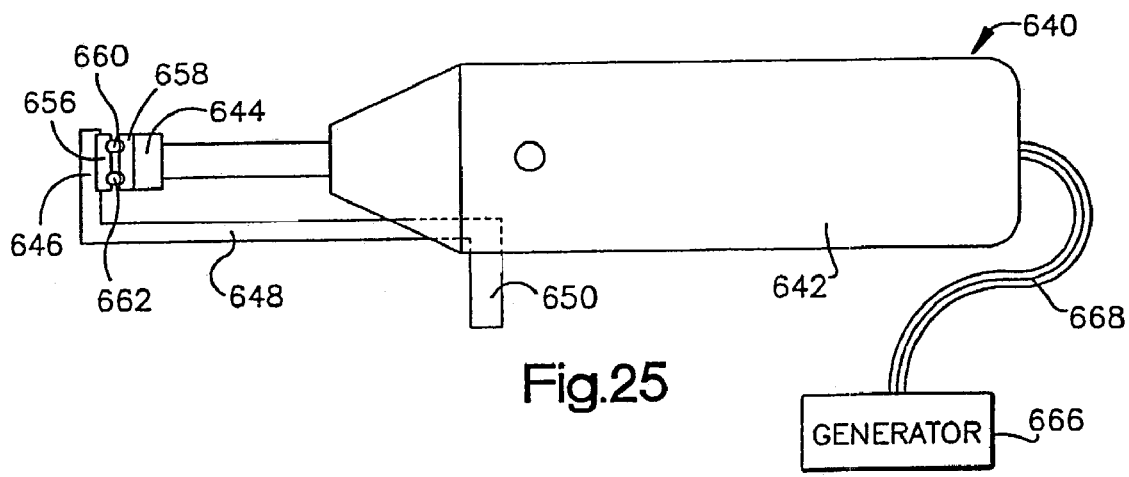
FIG. 25 is a schematic illustration of a second apparatus for applying ultrasonic vibratory energy to a suture retainer.

Embodiment of FIG. 25

In the embodiment of the invention illustrated in FIG. 25, the horn and anvil are disposed on a pair of members 602 and 604 which are pivotally interconnected. In the embodiment of the invention illustrated in FIG. 25, the horn and anvil of an ultrasonic energy application apparatus are movable relative to each other along a linear path.

The ultrasonic energy application apparatus 640 of FIG. 25 includes a handle 642. A horn 644 is connected with the handle 642. An anvil 646 is integrally formed as one piece with a member 648 which is movable along a linear path relative to the handle 642. An actuator member 650 is connected with the member 648 and is movable toward the left (as viewed in FIG. 25) to move the anvil 646 toward the horn 644.

Sections 660 and 662 of a suture are disposed between the sections 656 and 658 of the suture retainer. The suture retainer may have a construction similar to the construction of the suture retainer illustrated in FIG. 6.

A generator 666 is connected with the handle 642 by a cable 668. The cable 668 connects the generator 666 with a transducer which changes high frequency electrical energy conducted from the generator 666 to low amplitude mechanical vibration. These vibrations are transmitted to a booster. The vibrations are then transmitted to the horn. The horn applies the vibrations to the sections 658 of the suture retainer.

It should be understood that the ultrasonic energy application apparatus of FIGS. 24 and 25 could have any desired construction. It is contemplated that ultrasonic energy application apparatus which is commercially available from Dukane Corporation may be utilized. Of course, ultrasonic energy application apparatus which is commercially available from other sources may be used if desired. It should be understood that the suture retainers of FIGS. 1-23 may be utilized in association with any desired ultrasonic energy application apparatus.

Figure 26:
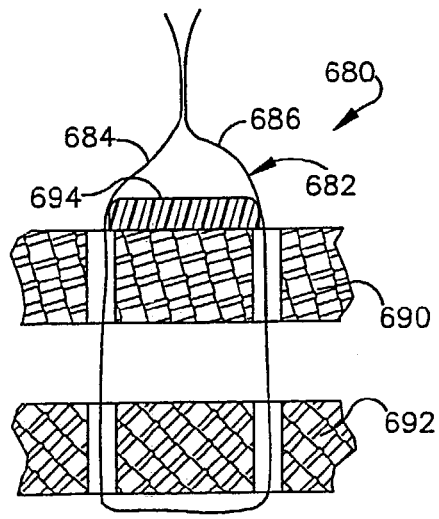
FIG. 26 is a schematic illustration, similar to FIG. 1, depicting the manner in which layers of body tissue are moved into linear apposition with each other and secured with a suture.
Figure 27:
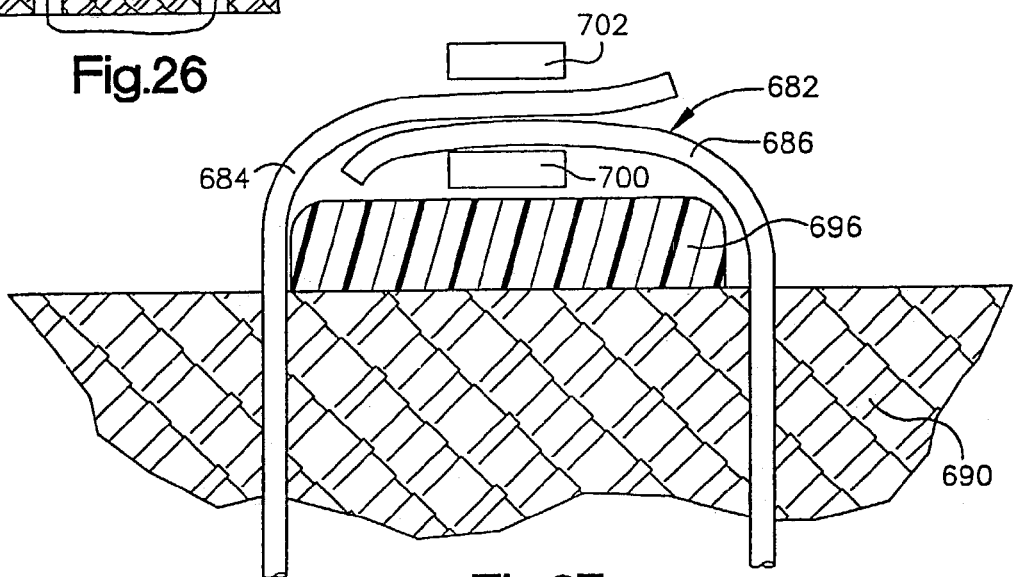
FIG. 27 is a schematic fragmentary sectional view illustrating the manner in which sections of the suture of FIG. 26 are positioned relative to each other and to apparatus which applies ultrasonic vibratory energy to the sections of the suture.
Figure 28:
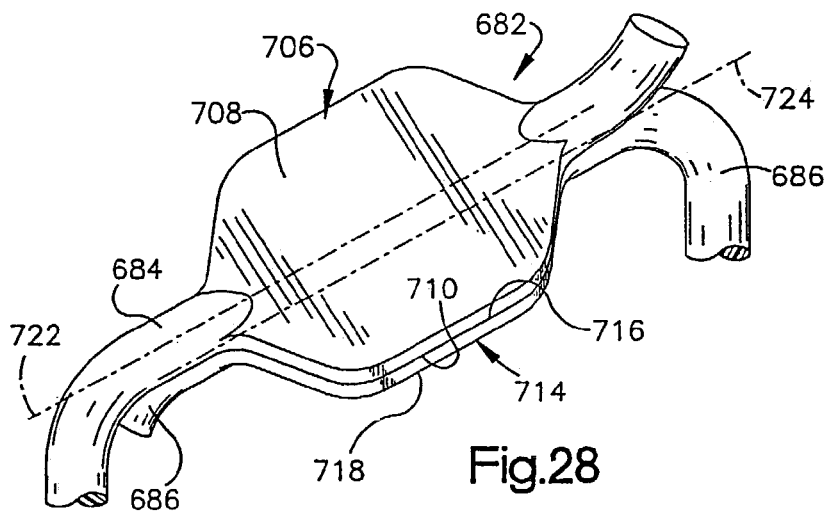
FIG. 28 is a schematic illustration depicting the manner in which sections of the suture of FIG. 27 are extended.

Embodiment of FIGS. 26-28

In the embodiments of the invention illustrated in FIGS. 1-22, a suture retainer has been utilized to interconnect sections of a suture. In the embodiment of the invention illustrated in FIGS. 26 through 28, the sections of the suture are directly connected to each other. Since the embodiment of the invention illustrated in FIGS. 26-28 is generally similar to the embodiments of the invention illustrated in FIGS. 1-22, similar terminology will be utilized to identify similar components. It should be understood that one or more of the features of other embodiments of the invention illustrated herein could be used with the embodiment of the invention illustrated in FIGS. 26-28.

A tissue securing system 680 (FIG. 26) includes a suture 682. The suture 682 includes left and right sections 684 and 686 which are interconnected without using a suture retainer. The two sections 684 and 686 may be knotted together and then interconnected. Alternatively, the two suture sections may just be interconnected, without knotting in the manner illustrated in FIGS. 27 and 28.

The tissue securing system 680 secures upper and lower layers 690 and 692 of soft, human body tissue in linear apposition with each other. Thus, the two layers 690 and 692 of human body tissue are approximated and held against movement relative to each other by a suture 682. Although the two layers 690 and 692 of human body tissue have been schematically illustrated in FIG. 26 as being spaced apart from each other, they are held in a side-by-side relationship with each other and pressed together by tightening the tissue securing system 680. Pressing the two layers 690 and 692 together with the tissue securing system 680 promotes healing of the tissue.

Although the tissue securing system 680 has been illustrated in FIG. 26 as being used to hold layers of soft tissue in linear apposition with each other, it is contemplated that the tissue securing system may be used in many different locations in a patient's body to secure tissue. For example, the tissue securing system 680 could be utilized to secure soft tissue such as a ligament or tendon against movement relative to a bone. Alternatively, the tissue securing system 680 could be utilized to interconnect portions of a flexible conduit, such as a blood vessel or intestine. It should be understood that the tissue securing system 680 may be used with either hard body tissue or soft body tissue or both hard and soft body tissue.

A force distribution member 694 is disposed between the two sections 684 and 686 of the suture 682. When the suture 682 is tensioned, the force distribution member 694 distributes the force over a relatively large area of the upper layer 690 of body tissue. Although only the force distribution member 694 is illustrated in FIG. 26 in association with the upper layer 690 of body tissue, a similar force distribution member could be provided in association with the lower layer 692 of body tissue if desired.

In accordance with a feature of this embodiment of the invention, the sections 684 and 686 of the suture 682 are interconnected without using a suture retainer similar to the suture retainers illustrated in FIGS. 1-22 herein. In the embodiment of the invention illustrated in FIGS. 26-28, the two sections 684 and 686 of the suture 682 are heated, flattened, and bonded together. Heating the suture sections 684 and 686 softens the material of the suture sections and allows them to be plastically deformed from a cylindrical configuration to a flat, generally planar configuration. Flattening the cylindrical sections 684 and 686 of the suture 682 increases the area at which the suture sections can be interconnected and thereby increases the strength of the connection between the suture sections.

The suture 682 may be formed of many different materials, including the materials previously mentioned herein. The suture 682 may be formed of either a biodegradable or a non-biodegradable material. It is believed that it will be preferred to form the suture 682 of a biodegradable material. It may be preferred to form the suture 682 of a biodegradable amorphous polymer. For example, the suture 682 could be formed of polyhydroxyalkanoate. Of course, the suture 682 could be formed of other materials if desired.

When the suture 682 is to be connected with the layers 690 and 692 of body tissue, the suture is positioned as illustrated schematically in FIG. 26. The sections 684 and 686 of the suture 682 are tensioned with a predetermined force. While the sections 684 and 686 of the suture are being tensioned, the force distribution member 694 is pressed against the upper layer 690 of body tissue. This results in the upper and lower layers 690 and 692 of the body tissue being compressed together with a predetermined force.

Once the layers 690 and 692 have been pressed together with a predetermined force by tensioning the sections 684 and 686 of the suture 682 and pressing the force distribution member 694 against the body tissue, the sections of the suture are interconnected. To interconnect the sections 684 and 686 of the suture 682, the two sections are pulled tight across the force distribution member and disposed in an overlapping relationship. An anvil 700 is positioned on one side of the two sections 684 and 686 of the suture 682. A horn 702 is positioned on the opposite side of the sections 684 and 686 of the suture 682. The anvil 700 and horn 702 are pressed against the opposite sides of the suture 682 with a predetermined force.

The suture sections 684 and 686 are stacked in a side-by-side relationship between the anvil 700 and horn 702. The anvil 700 engages one suture section and the horn 702 engages the other suture section. Thus, the anvil 700 may engage the suture section 684 and the horn 702 my engage the suture section 686.

While the sections 684 and 686 of the suture 682 are clamped between the anvil 700 and horn 702, ultrasonic vibratory energy is transmitted from the horn 702 to the sections 684 and 686 of the suture. At this time, the suture sections are tensioned with a predetermined force. The ultrasonic vibratory energy is at a frequency of between 20 kilohertz and 70 kilohertz. It is believed that it may be preferred to transmit ultrasonic vibratory energy to the sections of the suture 682 at a frequency of 70 kilohertz or more.

The ultrasonic vibratory energy transmitted from the horn 702 to the suture 682 is effective to heat the material of the suture into its transition temperature range. As the material of the suture 682 is heated into its transition temperature range, the material loses its rigidity and softens. However, the material of the suture 682 does not melt and become a liquid as it is heated into the transition temperature range.

The heated and softened material of the sections 684 and 686 of the suture 682 are flattened from the cylindrical configuration of FIG. 27 to form thin layers which are disposed in a side-by-side relationship and have a generally plate-like configuration which is illustrated schematically in FIG. 28. Thus, the section 684 of the suture is flattened to form a layer 706 having an upper major side surface 708 which extends parallel to a lower major side surface 710 of the layer 706. Similarly, the section 686 of the suture 682 is flattened to form a layer 714 having a flat upper major side surface 716 which extends parallel to a lower major side surface 718 of the layer 714.

As the section 684 of the suture 682 is flattened, it is extended sideways in opposite directions along a path which extends perpendicular to a central axis 722 (FIG. 28) of the suture section 684. Similarly, as the section 686 of the suture 682 is flattened, it is extended sideways in opposite directions along a path which extends perpendicular to a central axis 724 of the suture section 686. Although the flattened suture sections 684 and 686 have been illustrated as having planar major side surfaces 708, 710, 716 and 718, the suture sections could be flattened in such a manner as to have arcuately curving major side surfaces. For example, the major side surfaces 708, 710, 716 and 718 of the flattened suture sections 684 and 686 could curve upward (as viewed in FIG. 27) away from the body tissue 690.

The side surfaces 708, 710, 716 and 718 all have a relatively large area. The area of each unit of length as measured along a longitudinal central axes 722 and 724 of the suture sections at the side surfaces 708, 710, 716 and 718, is greater than the corresponding area of a unit of length of the section of the suture having the cylindrical configuration illustrated in FIG. 27.

Thus, a one-inch length of a cylindrical portion of the suture 682 has a circumferential area of pi (3.1416) times the diameter of the cylindrical section 684 of the suture 682. A one inch length, as measured along a longitudinal central axis 722 of the suture section 684, of the upper side surface 708 of the layer 706 has an area which is greater than pi (3.1416) times the diameter of the cylindrical portion of the suture 682. Similarly, a unit of length of the upper major side surface 716 of the layer 714 is greater than the area of a unit of length of the cylindrical portion of the suture 682.

When the sections 684 and 686 of the suture 682 have been heated and flattened from the cylindrical configuration of FIG. 27 to the plastically deformed and flattened configuration of FIG. 28 by the anvil 700 and horn 702, the application of ultrasonic vibratory energy to the layers 706 and 708 by the horn 702 is interrupted. As the material of the layers 706 and 714 cools, a secure bond is formed between the layers 706 and 714 throughout the extent of the lower major side surface 710 of the upper layer 706 and the upper major side surface 716 of the lower layer 714. The relatively large area of the bond between the two layers 706 and 714 provides a strong interconnection between the two suture sections 684 and 686.

In the foregoing description, the sections 684 and 686 were heated, under the influence of ultrasonic vibratory energy transmitted from the horn 702, and flattened to have surface areas which are greater than the surface area of a corresponding length of a cylindrical portion of the suture 682. However, it is contemplated that the sections 684 and 686 of the suture 682 could be flattened to a lesser extent. If this was done, the area of one of the major side surfaces, for example the lower major side surface 710 of the layer 706, might not be as great as the area of a corresponding length of a cylindrical portion of the suture 682. Thus, the sections 684 and 686 of the suture 682 may be flattened and extended sideways to a greater or lesser extent. Even a relatively small extent of flattening of the sections 684 and 686 of the suture 682 will result in an increase in the area at which the two sections of the suture are bonded together. This is because the circumferential extent of a bond formed between a pair of cylindrical surfaces disposed in tangential engagement is relatively small. The extent of the bond between the surfaces 710 and 716 is relatively large even though the surfaces have a smaller extent than illustrated in FIG. 28.

What is claimed is:

1. A method of securing a suture relative to body tissue comprising:
providing a suture retainer having
first and second portions;
positioning a suture through body tissue;
tensioning the suture;
positioning the suture between said first and second portions;
providing a first tool member having a rigid surface comprising an ultrasonic energy effector;
providing a second tool member having a rigid surface comprising a member selected from the group consisting of an anvil or an ultrasonic energy effector;
compressing said retainer by engaging said first portion with said first tool member and engaging said second portion with said second tool member, and compressing said first and second portions between said first and second tool members by bringing said first and second tool members towards each other with a predetermined force; and
applying ultrasonic energy to the suture retainer to thereby bond said first and second portions, whereby the suture is secured to the suture retainer.

2. The method according to claim 1 wherein three distinct planes are defined by the surface of engagement of said first tool member, the surface of engagement of said second tool member, and the surface of contact of the retainer with the body tissue.

3. The method according to claim 1 wherein the first portion of the suture retainer includes a first groove configured for receiving the suture, such that the suture is disposed in the first groove when the first and second portions of the suture retainer are compressed.

4. The method according to claim 3 wherein the second portion of the suture retainer includes a second groove configured for receiving the suture, the second groove is positioned opposite the first groove, such that the suture is disposed in the first and second grooves when the first and second portions of the suture retainer are compressed.

5. The method according to claim 3 wherein:
the suture includes first and second suture sections; and
the first portion of the suture retainer includes a second groove configured for receiving the suture, such that the first section of the suture is disposed in the first groove and the second section of the suture is disposed in the second groove when the first and second portions of the suture retainer are compressed.

6. The method according to claim 5 wherein the second portion of the suture retainer includes a third groove positioned opposite the first groove and a fourth groove positioned opposite the second groove, such that the first section of the suture is disposed in the first and third grooves and the second section of the suture is disposed in the second and fourth grooves when the first and second portions of the suture retainer are compressed.

7. The method according to claim 1 further comprising wrapping the suture around a center portion of the suture retainer.

8. The method according to claim 7 wherein the suture includes first and second suture sections, such that the first and second suture sections are wrapped about the center portion of the suture retainer.

9. The method according to claim 1 wherein the suture retainer includes a center portion interposed between the first and second portions and the center portion of the suture retainer is cylindrical in shape and includes a groove about the circumference of the cylindrical shape configured for receiving the suture.

10. The method according to claim 1 wherein the suture retainer includes a center portion interposed between the first and second portions and the first portion of the suture retainer includes a first groove and the center portion of the suture retainer includes a second groove opposite the first groove, such that the suture is disposed in the first and second grooves when the first and second portions of the suture retainer are compressed.

11. The method according to claim 10 wherein:
the suture includes first and second suture sections; and
the second portion of the suture retainer includes a third groove and the center portion of the suture retainer includes a fourth groove opposite the third groove, such that the first section of the suture is disposed in the first and second grooves and the second section of the suture is disposed in the third and fourth grooves when the first and second portions of the suture retainer are compressed.

12. The method according to claim 1 wherein the suture retainer includes a base section and at least one arm section defining at least one recess configured for receiving the suture.

13. The method according to claim 12 wherein positioning the suture between the first and second portions of the suture retainer includes;
   positioning the suture in the at least one recess; and
   compressing the at least one arm and base sections together.

14. The method according to claim 13 wherein the suture retainer includes a first arm section defining a first recess and a second arm section defining a second recess, with the first and second recesses on opposite sides of the base section.

15. The method according to claim 14 further comprising positioning a first suture section within the first recess and a second suture section within the second recess.

16. A method of securing a suture relative to body tissue comprising:
   providing a suture retainer including a first portion having exterior, interior, and bottom surfaces,
   a second portion having exterior, interior, and bottom surfaces,
   whereby said first portion interior surface and said second portion interior surface are disposed facing each other, thereby forming a gap therebetween;
   positioning a suture through body tissue;
   tensioning the suture;
   positioning the suture within the gap of the suture retainer;
   positioning said first portion bottom surface and said second portion bottom surface of the suture retainer in contact with the body tissue;
   transmitting a force from the suture retainer to the body tissue;
   providing a first tool member having a rigid surface comprising an ultrasonic energy effector;
   providing a second tool member having a rigid surface comprising a member selected from the group consisting of an anvil or an ultrasonic energy effector;
   compressing the suture retainer by engaging first portion exterior surface with said first tool member, and engaging said second portion exterior surface with said second tool member, and compressing the first and second portions between said first and second tool members by bringing said first and second tool members towards each other with a predetermined force; and
   applying ultrasonic energy to the suture retainer to thereby bond said first and second portions, whereby the suture is secured to the suture retainer;
   wherein the direction of force with which said first and second tool members are brought together is generally orthogonal to the direction of force applied by the suture retainer to the body tissue, and
   wherein the force with which said first and second tool members are brought together is independent of the force applied by said retainer to the body tissue.

17. The method according to claim 16 wherein the first portion of the suture retainer includes a first groove configured for receiving the suture, such that the suture is disposed in the first groove when the first and second portions of the suture retainer are compressed.

18. The method according to claim 17 wherein the second portion of the suture retainer includes a second groove configured for receiving the suture, the second groove is positioned opposite the first groove, such that the suture is disposed in the first and second grooves when the first and second portions of the suture retainer are compressed.

19. The method according to claim 17 wherein:
   the suture includes first and second suture sections; and
   the first portion of the suture retainer includes a second groove configured For receiving the suture, such that the first section of the suture is disposed in the first groove and the second section of the suture is disposed in the second groove when the first and second portions of the suture retainer are compressed.

20. The method according to claim 19 wherein the second portion of the suture retainer includes a third groove positioned opposite the first groove and a fourth groove positioned opposite the second groove, such that the first section of the suture is disposed in the first and third grooves and the second section of the suture is disposed in the second and fourth grooves when the first and second portions of the suture retainer are compressed.

21. The method according to claim 16 further comprising wrapping the suture around a center portion of the suture retainer.

22. The method according to claim 21 wherein the suture includes first and second suture sections, such that the first and second suture sections arc wrapped about the center portion of the suture retainer.

23. The method according to claim 16 wherein a center portion of the suture retainer is cylindrical in shape and includes a groove about the circumference of the cylindrical shape configured for receiving the suture.

24. The method according to claim 16 wherein the first portion of the suture retainer includes a first groove and a center portion of the suture retainer includes a second groove opposite the first groove, such that the suture is disposed in the first and second grooves when the first and second portions of the suture retainer are compressed.

25. The method according to claim 24 wherein:
   the suture includes first and second suture sections; and
   the second portion of the suture retainer includes a third groove and the center portion of the suture retainer includes a fourth groove opposite the third groove, such that the first section of the suture is disposed in the first and second grooves and the second section of die suture is disposed in the third and fourth grooves when the first and second portions of the suture retainer are compressed.

26. A method of securing a suture relative to body tissue, comprising:
   providing a suture retainer including a base section, at least one arm section defining at least one recess configured for receiving the suture, and a tissue contacting surface, a portion of the base section and a portion of the at least one arm section being generally perpendicular to the tissue contacting surface;
   positioning the suture through first and second layers of body tissue;
   tensioning the suture;
   positioning the suture in the at least one recess;
   positioning the tissue contacting surface of the suture retainer in contact with at least one of the first and second layers of body tissue;
   transmitting a force from the suture retainer to the body tissue, such that the first and second layers of body tissue are in proximal relationship;
   providing a tool having a first tool member having a rigid surface comprising an ultrasonic energy effector, and a second tool member having a rigid surface comprising a member selected from the group consisting of an anvil or an ultrasonic energy effector
   compressing the at least one arm and base sections together by engaging said at least one arm section with one of said first or second tool member, and engaging said base section with the other of said first or second tool member and compressing said at least one arm section and said base section between said first and second tool members by bringing said first and second tool members towards each other with a predetermined force; and applying ultrasonic energy to the suture retainer to thereby bond said at least one arm and base sections, whereby the suture is secured to the suture retainer.

27. The method according to claim 26 wherein the suture retainer includes a first and section defining a first recess and a second arm section defining a second recess, wherein the first and second recesses are on opposite sides of the base section.

28. The method according to claim 27 further comprising positioning a first suture section within the first recess and a second suture section within the second recess.

29. The method of claim 1, wherein said first tool member and said second tool member arc portions of a single tool.

30. The method of claim 1, wherein force with which said first and second tool members are brought together is not communicated to the body tissue.

* * * * *

UNITED STATES PATENT AND TRADEMARK OFFICE
CERTIFICATE OF CORRECTION

PATENT NO.         : 7,429,266 B2                                              Page 1 of 1
APPLICATION NO. : 10/458117
DATED              : September 30, 2008
INVENTOR(S)        : Peter M. Bonutti It is certified that error appears in the above-identified patent and that said Letters Patent is hereby corrected as shown below:

Column 49, line 67 Claim 19 Change "For" to --for--

Column 50, line 18 Claim 22 Change "arc" to --are--

Column 52, line 5 Claim 29 Change "arc" to --are--

Signed and Sealed this

Seventeenth Day of March, 2009

JOHN DOLL
*Acting Director of the United States Patent and Trademark Office*